＊

US006204060B1

(12) United States Patent
Mehtali et al.

(10) Patent No.: US 6,204,060 B1
(45) Date of Patent: *Mar. 20, 2001

(54) VIRAL VECTORS AND LINE FOR GENE THERAPY

(75) Inventors: Majid Mehtali, Illkirch-Graffenstaden (FR); Monika Lusky, Freiburg (DE); Karola Rittner, Strasbourg (FR)

(73) Assignee: Transgene S.A., Strasbourg (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,562

(22) PCT Filed: Jul. 24, 1996

(86) PCT No.: PCT/FR96/01165

§ 371 Date: Mar. 31, 1997

§ 102(e) Date: Mar. 31, 1997

(87) PCT Pub. No.: WO97/04119

PCT Pub. Date: Feb. 6, 1997

(30) Foreign Application Priority Data

Jul. 24, 1995 (FR) .................................................. 95 08946
Apr. 9, 1996 (FR) .................................................. 96 04413

(51) Int. Cl.$^7$ ............................. C12N 15/86; C12N 5/10; C12N 15/63
(52) U.S. Cl. ...................... 435/456; 435/320.1; 435/325; 435/366; 435/369; 435/370
(58) Field of Search ............................... 435/69.1, 172.1, 435/172.3, 320.1, 325, 366, 369, 370, 455, 456; 424/93.2, 93.6

(56) References Cited

FOREIGN PATENT DOCUMENTS 9428152  12/1994  (WO) .
9502697   1/1995  (WO) .

OTHER PUBLICATIONS

Gene Therapy, Mar. 1995, pp. 124–131, Hersh et al, "Modulation of gene expression after replication–deficient, recombinant adenovirus–mediated gene transfer by the product of a second adenovirus vector".
Journal of Virology, Apr. 1995, pp. 2565–2573, Kim et al, "Tetracycline Repressor–Regulated Gene Repression in Recombinant Human Cytomegalovirus".
Molecular and Cellular Biology, Apr. 1995, pp. 1907–1914, Deuschle et al, "Tetracycline–Reversible Silencing of Eukaryotic Promoters".

Nucleic Acids Research, vol. 19, No. 23, pp. 6579–6586, O'Connor et al, "The C–terminal 70 amino acids of the adenovirus E4–ORF6/7 protein are essential and sufficient for E2F complex formation".
Virus Genes (1990), vol. 4, No. 1, pp. 53–61, Roovers et al, "Physical Mapping of Two Temperature–Sensitive Adenovirus Mutants Affected in the DNA Polymerase and DNA Binding Protein".
Molecular and Cellular Biology, Dec. 1994, vol. 14, No. 12, pp. 8166–8173, Shan et al, "Deregulated Expression of E2F–1 Induces S–Phase Entry and Leads to Apoptosis".
Journal of Clinical Investigation, Apr. 1994, vol. 93, pp. 1864–1868, Fishman et al, "Tetracycline–regulated Cardiac Gene Expression in Vivo".
Human Gene Therapy, Dec. 1995, vol. 6, pp. 1575–1586, Krougliak et al, "Development of Cell Lines Capable of Complementing E1, E4, and Protein IX Defective Adenovirus Type 5 Mutants".
Cancer Gene Therapy, 1995, XP000568385, Wang et al, "A new packaging cell line for propagation of the second generation of the recombinant adeno virus vector".
Rabinovich et al., Science, vol. 265, pp. 1401–1404, Sep. 2, 1994.*
Orkin et al., "Report and Recommendations of the Panel to Assess the NIH Investment in Research on Gene Therapy", Dec. 7, 1995.*
Tanaka et al., Cancer Research, vol. 56, pp. 1341–1345, Mar. 15, 1996.*
Siders et al., Cancer Research, vol. 56, pp. 5638–5646, Dec. 5, 1996.*
Richard C. Boucher, TIG, vol. 12, No. 3, pp. 81–84, Mar. 1996.*
Zhang et al., PNAS, vol. 93, pp. 4513–4518, Apr. 1996.*
Ion Cohen, Science, vol. 265, pp. 1371–1373, Sep. 2, 1994.*
Michael B.A. Oldstone, Virology, vol. 234, pp. 179–185, 1997.*

* cited by examiner

*Primary Examiner*—David Guzo
(74) *Attorney, Agent, or Firm*—Burns, Doane, Swecker & Mathis, L.L.P.

(57) ABSTRACT

Novel viral vectors in which the expression of viral genes is regulated in such a way that it is functional in a complementation cell and non-functional in a host cell, as well as viral particles and host cells containing said novel vectors, are disclosed. A complementation cell including a viral gene expression regulator, and a method for preparing infectious viral particles, are also disclosed. Finally, a pharmaceutical composition containing said vectors, and the therapeutical use thereof, are disclosed.

42 Claims, 12 Drawing Sheets

VIRAL VECTORS AND LINE FOR GENE THERAPY

The present invention relates to new viral vectors permitting the transfer and expression of genes of interest in a host cell or body, the expression of the viral genes being regulated so as to be functional in a complementation cell and nonfunctional in the host cell or body. It also relates to the cells containing these new vectors, as well as to a method for preparing infectious viral particles intended for therapeutic use. The invention is of very special interest in relation to prospects for gene therapy, in particular in man.

The possibility of treating human diseases by gene therapy has changed in a few years from the stage of theoretical considerations to that of clinical applications. The first protocol applied to man was initiated in the U.S. in September 1990 on a patient who was genetically immunodeficient as a result of a mutation affecting the gene coding for adenine deaminase (ADA). The relative success of this first experiment encouraged the development of new gene therapy protocols for various genetic or acquired diseases (infectious diseases, and viral diseases in particular, such as AIDS, or cancers). The large majority of the protocols described hitherto employ viral vectors to transfer the therapeutic gene to the cells to be treated and to express it therein.

To date, retroviral vectors are among the ones most widely used on account of the simplicity of their genome. However, apart from their restricted capacity for cloning, they present two major drawbacks which limit their systematic use: on the one hand they chiefly infect dividing cells, and on the other hand, as a result of their integration at random in the genome of the host cell, the risk of insertional mutagenesis is not insignificant. For this reason, many scientific teams have endeavored to develop other types of vector, among which those originating from adenoviruses, adeno-associated viruses (AAV), cytomegaloviruses, poxviruses and herpesviruses may be mentioned. Generally speaking, their organization and their infection cycle are amply described in the literature available to a person skilled in the art.

In this connection, the use of adenoviral vectors has been seen to be a promising alternative. Adenoviruses have been demonstrated in many animal species, have a broad host range, have little pathogenicity and do not present the drawbacks associated with retroviruses since they are non-integrative and replicate also in resting cells. As a guide, their genome consists of a linear, double-stranded DNA molecule of approximately 36 kb carrying more than about thirty genes, both early genes necessary for viral replication and late structural genes (see FIG. 1).

The early genes are divided into 4 regions dispersed in the adenoviral genome (E1 to E4; E standing for early). They contain 6 transcription units which possess their own promoters. The late genes (L1 to L5; L standing for late) partially overlap the early transcription units and are, for the most part, transcribed from the major late promoter (MLP).

At the present time, all the adenoviral vectors used in gene therapy protocols lack most of the E1 region essential for replication, in order to avoid their dissemination in the environment and the host body. Some of them contain additional deletions, in particular in the nonessential E3 region, enabling their cloning capacity to be increased. The genes of interest are introduced into the viral DNA in place of one or other deleted region. Deletion of the E1 region renders the viral genome deficient for replication. However, E1$^-$ viruses may be propagated in a complementation cell line, which supplies in trans the deleted viral functions to generate an infectious viral particle. Line 293, established from human embryonic kidney cells, which complements the E1 function effectively (Graham et al., 1977, J. Gen. Virol. 36, 59–72), is commonly used. The E3 region is nonessential and does not need to be complemented.

While the feasibility of gene transfer using these first generation vectors is now well established, the question of their safety remains unresolved. Apart from the safety aspects (risk of generating RCAs, that is to say replication competent particles), the problem of their toxicity arises. In effect, the first clinical trials have revealed the induction of inflammatory responses associated with the expression of the viral genes in the host.

Second generation adenoviral vectors have recently been proposed in the literature. They retain the in cis regions necessary for replication of the virus in the infected cell (ITRs and encapsidation sequences) and contain substantial internal deletions aimed at abolishing the bulk of the viral genes whose expression in vivo is not desirable. However, these vectors of the prior art have some drawbacks which limit their exploitation at an industrial level. It is, in effect, necessary to have at one's disposal new lines complementing the collective deleted functions and enabling viral particles to be produced at a high titer. In point of fact, such a line, in order to be optimal in terms of capacity for growth and yield of viral particles, is especially difficult to generate on account of the cytotoxicity of the adenoviral genes.

The present invention enables these drawbacks to be remedied. On the one hand, a new line derived from line 293 complementing the E1 and E2 or E4 adenoviral functions, for the amplification of conventional second generation adenoviral vectors, has now been constructed, in which line the expression of the E2 or E4 regions is directed by a promoter equipped at its 5' end with so-called "operator" sequences of the bacterial tetracycline operon, these sequences hereinafter being designated tet O. The synthesis of the corresponding expression products will be activated only in the presence of an inducer which can be produced by the adenoviral vector or by the line itself. Similarly, a repressor may be added to the culture medium when complementation is no longer desired.

On the other hand, new adenoviral vectors from which the majority of the E1 and E3 regions have been deleted have now been generated, in which vectors the transcription units of the remaining viral regions (E2, E4 and/or L1–L5) are regulable with the object of permitting their expression when infectious viral particles are to be generated and of inhibiting it in the host cell. In the examples which follow, the regulation is effected by the tet O sequences. Their insertion on the 5' side of the TATA box generates a promoter from which the baseline level of transcription is minimal but may be strongly stimulated in the presence of the inducer mentioned above. Thus, the production of viral proteins is activated in a 293 line expressing the inducer, which will enable infectious viral particles to be formed. In contrast, it is considerably reduced in the infected host cell which does not naturally produce the inducer of bacterial origin. The regulation of the viral genes has no effect on the expression of the exogenous nucleotide sequence placed under the control of a promoter that does not respond to tetracycline.

The adenoviral vectors of the present invention provide an advantageous approach to the drawbacks inherent in the use of the vectors of the prior art, since they combine safety of use and ease of production. On the one hand they may be propagated in a conventional complementation line with a high titer compatible with industrial requirements, and on the other hand they enable an exogenous nucleotide sequence to be transferred in vivo, and to be expressed stably while limiting the adverse effects (inflammatory responses in the host). They are most especially suitable for human gene therapy.

Accordingly, the subject of the present invention is a viral vector, characterized in that it comprises an expression unit containing one or more viral genes; said expression unit being functional in a complementation cell and nonfunctional in a host cell.

For the purposes of the present invention, a "viral vector" is obtained from a parent virus whose genome has been modified. These modifications may be diverse (deletion, mutation and/or addition of one or more nucleotides) and localized in the coding regions of the viral genome or outside these regions, for example in the promoter regions. As a guide, some viral sequences may be deleted, rendered nonfunctional or replaced by other sequences, and in particular an exogenous nucleotide sequence whose expression is sought in a host cell.

A viral vector according to the invention may be derived from a wide variety of viruses, such as herpesviruses, cytomegaloviruses, AAV (adeno-associated virus) and poxviruses, and in particular vaccinia, fowlpox or canarypox virus. Such vectors, as well as the techniques for preparing them, are known to a person skilled in the art.

However, a vector which is especially suitable for the present invention is an adenoviral vector. It may be derived from an adenovirus of human, canine, avian, bovine, murine, ovine, porcine or simian origin, or alternatively from a hybrid comprising adenoviral genome fragments of different origins. The adenoviruses CAV-1 or CAV-2 of canine origin, DAV of avian origin or alternatively Bad type 3 of bovine origin (Zakharchuk et al., 1993, Arch. Virol., 128, 171–176; Spibey and Cavanagh, 1989, J. Gen. Virol., 70, 165–172; Jouvenne et al., 1987, Gene, 60, 21–28; Mittal et al., 1995, J. Gen. Virol., 76, 93–102) may be mentioned more especially. However, an adenoviral vector derived from a human adenovirus, preferably of serotype C and, as an absolute preference, of type 2 or 5 (Graham and Prevect, 1991, Methods in Molecular Biology, vol. 7, p 109–128; Ed: E. J. Murey, The Human Press Inc.), will be preferred.

An advantageous embodiment of the present invention consists of a vector which is defective for replication, in which one or more viral genes necessary for replication are deleted or rendered nonfunctional. Such a vector, incapable of autonomous replication, will be propagated in a complementation cell. The term "complementation cell" denotes a cell capable of supplying in trans the function(s) for which a vector according to the invention is defective. In other words, it is capable of producing the proteins(s) necessary for the replication and encapsidation of said vector, early and/or late proteins, which it cannot itself produce and which are necessary for the formation of an infectious viral particle. By way of illustration, since a preferred adenoviral vector according to the invention lacks most of the E1 region, use will be made of a complementation cell such as line 293, capable of supplying in trans the collective proteins encoded by the E1 region which the vector cannot produce. "Infectious viral particle" is understood to mean a viral particle having the capacity to infect a host cell and to cause the viral genome to enter the latter.

According to a preferential embodiment, a viral vector according to the invention is recombinant. Thus, it will comprise an exogenous nucleotide sequence placed under the control of the elements necessary for its expression in a host cell. "Exogenous nucleotide sequence" refers to a nucleic acid which can be of any origin and which is not normally present in the genome of a parent virus employed in the present invention or, if it is present, in a different genomic context. In the context of the invention, the exogenous nucleotide sequence perhaps [sic] made up of one or more genes, and especially gene(s) of therapeutic interest.

Generally speaking, the exogenous nucleotide sequence can code for an antisense RNA and/or an mRNA which will then be translated into a protein of interest. It may be of the genomic type, of the complementary DNA (cDNA) type or of mixed type (minigene, in which at least one intron is deleted). It may code for a mature protein or a precursor of a mature protein, in particular a precursor intended to be secreted and comprising a signal peptide. Moreover, the encoded product may be all or part of a protein as found in nature (native or truncated protein), or alternatively a chimeric protein originating from the fusion of sequences of diverse origin or else a mutated protein displaying improved and/or modified biological properties. Such proteins may be obtained by the conventional techniques of molecular biology.

In the context of the present invention, it can be advantageous to use the genes coding for the following polypeptides:

cytokines or lymphokines (interferons α, β and γ, interleukins and in particular IL-2, IL-6, IL-10 or IL-12, tumor necrosis factors (TNF), colony stimulating factors (GM-CSF, C-CSF, M-CSF, etc.);

cell or nuclear receptors (receptors recognized by pathogenic organisms (viruses, bacteria or parasites), and preferably by the HIV virus (human immunodeficiency virus) [lacuna] or their ligands;

proteins involved in a genetic disorder (factor VII, factor VIII, factor IX, dystrophin or minidystrophin, insulin, CFTR (cystic fibrosis transmembrane conductance regulator) protein, growth hormones (HGF) [lacuna];

enzymes (urease, renin, thrombin, etc.);

enzyme inhibitors (α1-antitrypsin, antithrombin III, inhibitors of viral proteases, etc.);

polypeptides having an antitumor effect capable of at least partially inhibiting the initiation or progression of tumors or cancers (antisense RNAs, antibodies, inhibitors acting on cell division or on transduction signals, expression products of tumor suppressing genes, for example p53 or Rb, proteins that stimulate the immune system, etc.);

proteins of the major histocompatibility complex classes I or II, or regulatory proteins that act on the expression of the corresponding genes;

polypeptides capable of inhibiting a viral, bacterial or parasitic infection and/or its development (antigenic polypeptides having immunogenic properties, antigenic epitopes, antibodies, trans-dominant variants capable of inhibiting the action of a native protein by competition, etc.);

toxins (herpes simplex virus 1 thymidine kinase (HSV-1 TK), ricin, cholera or diphtheria toxin, etc.) or immunotoxins; and markers (β-galactosidase, luciferase, etc.).

It should be pointed out that this list is not limiting and that other genes may also be employed.

Moreover, an exogenous nucleotide sequence employed in the present invention may comprise, in addition, a selectable gene enabling the transfected cells to be selected or identified. There may be mentioned the neo gene (coding for neomycin phosphotransferase) conferring resistance to the antibiotic G418, the dhfr (dihydrofolate reductase) gene, the CAT (chloramphenicol acetyltransferase) gene, the pac (puromycin acetyltransferase) gene or alternatively the gpt (xanthine guanine phosphoribosyltransferase) gene. Generally speaking, the selectable genes are known to a person skilled in the art.

Elements necessary for the expression of an exogenous nucleotide sequence in a host cell are understood to mean the collective elements permitting its transcription into RNA (antisense RNA or mRNA) and the translation of an mRNA into protein. Among these, the promoter assumes special importance. It may be isolated from any gene of eukaryotic or even viral origin, and may be constitutive or regulable. Alternatively, it can be the natural promoter of the gene in question. It will be preferable to employ a promoter different from the one included in the unit for the expression of the viral genes (defined below). Moreover, it may be modified so as to improve the promoter activity, to abolish a region that inhibits transcription, to render a constitutive promoter regulable or vice versa, to introduce a restriction site, etc. There may be mentioned, by way of examples, the promoters of the HSV-1 TK, murine or human PGK (phosphoglycerate kinase), $\alpha$1-antitrypsin (liver-specific) and immunoglobulin (lymphocyte-specific) genes, the SV40 virus (simian virus 40) early promoter, a retroviral LTR or alternatively the adenoviral MLP promoter, in particular of human adenovirus type 2.

Naturally, an exogenous nucleotide sequence employed in the present invention can, in addition, comprise further elements necessary for expression (intron sequence, signal sequence, nuclear localization sequence, transcription termination sequence, translation initiation site of the IRES or an other type, etc.) or alternatively for its maintenance in the host cell. Such elements are known to a person skilled in the art.

As stated above, a viral vector according to the present invention comprises an expression unit containing one or more viral genes and having the advantageous feature of being functional in a complementation cell and nonfunctional in a host cell. "Functional" is understood to mean an expression of the viral genes in a sufficient amount and for a sufficiently long time to permit the formation of an infectious viral particle. "Nonfunctional" is understood to mean an expression of the viral genes which is reduced (preferably by a factor of at least 10, or even a zero expression) relative to their level of expression in the parent virus. The functional character manifests itself in the production of the products of the viral genes included in the expression unit, it being possible for these products to be demonstrated by the standard techniques of molecular biology, immunology, biochemistry or enzymology. The nonfunctional character manifests itself in the absence of production or alternatively in the production of the viral products at a reduced level.

Advantageously, said expression unit comprises one or more heterologous regulatory sequence(s) not present in the parent viral DNA. Use may be made of sequences that respond to a regulator of the repressor type acting negatively on the expression, or preferably to a regulator of the inducer type exerting a positive action. A regulatory sequence employed in the context of the present invention may be of any origin, viral, prokaryotic or alternatively eukaryotic.

Generally speaking, regulatory sequences are described in the literature available to a person skilled in the art. It is also possible to employ a homolog whose sequence is modified relative to the native sequence but which exerts a similar or improved regulatory function. These modifications may result from the addition, deletion and/or replacement of one or more nucleotides.

In accordance with the objectives pursued by the present invention, a regulatory sequence is capable of modulating the expression of the viral genes at different levels: transcription, elongation, transport, stability of the mRNAs or alternatively translation. It may be present at various places in said expression unit, for example in the promoter, especially when its effect lies at transcriptional level (preferably upstream of the TATA box, up to a few hundred base pairs from the latter), or in the transcribed (and if possible noncoding) sequences when its action is exerted at a subsequent step of the transcription. It is possible to employ from 1 to 25 regulatory sequences, advantageously from 1 to 20, preferably from 1 to 10 and, as an absolute preference, from 1 to 7.

For the purposes of the present invention, the term "inducer" denotes a molecule which has the capacity of initiating or activating the expression of the viral genes placed under the control of a regulatory sequence, either directly by binding to said regulatory sequence, or indirectly via other cellular or viral factors. It can also prevent the action of a repressor. In contrast, a "repressor" has the capacity to inhibit or block the expression of the viral genes placed under the control of a regulatory sequence on which it acts, this taking place either directly or indirectly.

These definitions may be illustrated by the example of the lactose (lac) operon. The lac1 gene codes for a repressor which binds to a short regulatory sequence termed "operator", thereby preventing the transcription of the structural genes coding for the enzymes of the metabolic pathway of lactose. In the presence of the inducer, the latter binds to the repressor and converts it to an inactive form which can no longer bind to the operator, thereby enabling transcription to take place.

It is also possible to envisage using portions or analogs of these regulators in order to improve their efficacy or modify their specificity (for example anhydrotetracycline, ten times as effective as tetracycline for inhibiting transcription from a promoter comprising the regulatory sequences derived from the tetracycline operon, or the reverse transactivator described recently by Gossen et al., 1995, Science, 268, 1766–1769). Moreover, a regulator employed in the present invention can be a hybrid protein originating from the fusion of polypeptides of different origins. A preferred combination consists of a polypeptide capable of recognizing or binding a regulatory sequence employed in the present invention (for example derived from the tetracycline repressor (tet R) or estrogen repressor ER) and a polypeptide capable of activating expression (for example the activation domain of the Gal4 or VP16 proteins, capable of interacting with transcription factors).

Table 1 below lists some of the regulatory sequences and regulators which can be used in the context of the present invention:

| Origin of the regulaotry sequences | Inducer (+)/ Repressor (−) | Insertion site ☐ | Bibliographic reference |
|---|---|---|---|
| MRE (metal-responsive element) metallothionein gene | metal ions (+) | 5' TATA | Makarov et al., 1994, Nucleic Acid Res. 22, 1504–1505 |

-continued

| Origin of the regulaotry sequences | Inducer (+)/ Repressor (−) | Insertion site □ | Bibliographic reference |
|---|---|---|---|
| tryptophan operon | tryptophan (−) | 5' TATA | Yanofsky et al., 1981, Nucleic Acids Res. 9 6647–6668 |
| lac operator | product of the lacI gene (−) | 5' TATA | Miller and Reznikoff (Eds), The operons (Cold Spring Harbor Laboratory, New York [lacuna] |
| tet operator | VP-16 TetR protein (+) | 5' TATA | Gossen and Bujard, 1992, Proc. Natl. Acad. Sci. USA 89, 5547–5551 |
| tet operator | TetR(−) | 3' TATA | Kim, 1995, J. Viron. 69, 2565–2573 |
| TAR (transactivation responsive region) | TAT (+) | transcribed 5' sequence | Steffy and Wond-Staal, 1991, Microbiological Reviews 55, 193–205 |
| RRE (REV responsive element) | REV (+) | transcribed 3' sequence | Steffy and Wong-Staal, 1991, Microbiological Reviews 55, 193–205 |
| GRE (glucocorticoid responsive element) | glucocorticoid (+) | 5' TATA | Israel and Kaufman, 1989, Nucleic Acid Res. 17, 4589–4604 |
| Pre (progesterone responsive element) | progesterone (+) | 5' TATA | Gronemeyer et al., 1987, EMBO J. 6, 3985–3994 |
| Gal4 UAS (Gal 4 upstream activating sequence) | Gal4 (+) | 5' TATA | Webster et al., 1988, Cell 52, 169–178 |
| ERE (estrogen responsive element) | Estrogen (+) | 5' TATA | Klein-Hitpaβ et, al., 1986, Cell 46, 1053–1061 |

□ The insertion site is given only as a guide but without implied limitation

According to a particular embodiment of the present invention, regulatory sequences derived from the bacterial tetracycline operon, designated in the literature "operator" (tet O), are used. Generally speaking, the tetracycline resistance operon is encoded by the transposon Tn10 (Hillen et al., 1984, J. Mol. Biol. 172, 185–201). Regulation is effected by a short nucleotide sequence termed "operator" (tet O) which constitutes a binding site for various regulators. Thus, the binding of the tetacycline [sic] repressor (tet R) or of the antibiotic tetracycline considerably decreases the level of transcription. On the contrary, an activation effect is obtained by employing a protein, designated in the literature "tetracycline transactivator (tTA)", which results from the fusion between tet R and the 130 C-terminal amino acids of the activation domain of the VP16 protein of the herpes simplex virus. Gossen and Boujard (1992, Proc. Natl. Acad. Sci. USA 89, 5547–5551) have recently shown that this regulatory system is functional in eukaryotic cells. The expression of a reporter gene placed under the control of several copies of tet O upstream of basic transcription sequences (TATA box, transcription startsite, etc.) is detectable by coexpression of tTA and inhibited by the addition of tetracycline. Kim's group (1995, J. Virol. 69, 2565–2573), for its part, utilizes the tet O sequences positioned downstream of the TATA box of a promoter, and in this case transcription is inhibited by the action of tetR.

In the context of the present invention, the combination "tet O-minimal promoter" (in the 5' to 3' direction), giving rise to a promoter whose baseline transcription level is naturally very low but activable by the inducer tTA and repressible by tetracycline, is most especially preferred. However, it is also possible to use a promoter in which the tet O sequences are placed on the 3' side of the TATA box, or alternatively on each side of the latter, and which is repressible by a repressor comprising the sequences of tet R that recognize tet O.

As regards the preferred variant, an adenoviral vector according to the invention preferably consists of the genome of an adenovirus lacking all or part of the E1 region and, alternatively, all or part of the E3 region. Advantageously, it is preferable to retain a portion of the E3 region, and in particular the portion corresponding to the gene coding for the gp19k (Gooding and Wold, 1990, Critical Reviews of Immunology 10, 53–71), said portion not being included in an expression unit as defined above but placed under the control of a conventional homologous (E3) or heterologous promoter. It is self-evident that it is possible to carry out other modifications of the viral genome, in particular in the E4 or E2 region. It may be advantageous to introduce mutations or additional deletions. To illustrate this point, the temperature-sensitive mutation affecting the DBP (standing for DNA binding protein) gene of the E2A region (Ensinger and Ginsberg, 1972, J. Virol. 10, 328–339).

According to a preferential embodiment, an adenoviral vector according to the invention comprises an expression unit containing one or more viral genes of the E2, E4 or L1–L5 regions. An advantageous variant consists in retaining from the E4 region only the sequences coding for ORFs 3, 6 and/or 7 (these limited deletions of the E4 region not necessitating complementation of the E4 function; Ketner et al., 1989, Nucleic Acids Res. 17, 3037–3048).

It can also be advantageous to have at one's disposal an adenoviral vector comprising several expression units, it being possible to envisage all the combinations (E2 and E4, E2 and L1–L5, E4 and L1–L5 or E2, E4 and L1–L5). Regulatory sequences acting in the same manner, and preferably positively (for example TAR, RRE, tet O, etc.), will then be chosen. For reasons of simplicity of implementation, preference is given to the case where the units carry identical regulatory sequences enabling the adenoviral vector to be propagated in a complementation line comprising a single inducer.

The invention also relates to an infectious viral particle, as well as to a eukaryotic host cell comprising a viral vector according to the invention. Said host cell is advantageously a mammalian cell, and preferably a human cell, and can comprise said vector in integrated form in the genome or in nonintegrated form (episome). It can be a primary or tumor cell of hematopoietic (totipotent stem cell, leukocyte, lymphocyte, monocyte or macrophage, etc.), muscular, pulmonary, hepatic, epithelial or fibroblast origin.

The subject of the present invention is also a complementation cell, characterized in that it comprises an inducer and/or a repressor (regulator). Depending on the requirements, the latter may be added to the culture medium, or produced stably or transiently by the cell itself. Preferably, a complementation cell according to the invention is modified by the introduction of a DNA fragment coding for said regulator. All standard means for introducing a nucleic acid (synthetic, viral or plasmid vector, naked DNA, etc.) into a cell may be used in the context of the present invention, such as, for example, transfection, electroporation, microinjection, lipofection, adsorption and protoplast fusion. In the context of the invention, it can be advantageous to generate a complementation cell which produces only a single regulator, and in particular an inducer. However, it can also be advantageous to have at one's disposal cells producing several inducers.

According to an advantageous embodiment, a complementation cell according to the invention is capable of complementing in trans a viral vector according to the invention, and especially an adenoviral vector. In this connection, a complementation cell for the E1 and/or E4 function will advantageously be chosen. Accordingly, the invention also relates to a cell intended for the complementation of a second generation adenoviral vector which is defective for the E1 function and another adenoviral function (late or early). Such a cell comprises all or part of the E1 region of an adenovirus whose expression is controlled by any promoter, and all or part of a region of an adenovirus other than the E1 region, placed under the control of a promoter equipped with regulatory sequences, for example at its 5' end with at least one and preferably one to 20 tet O sequence(s) which is/are activable by the transactivator tTA. An advantageous variant consists of a minimal promoter derived from the CMV virus (cytomegalovirus), upstream of which lie 7 tet O sequences in a head-to-tail orientation. The inducer may be introduced into the complementation cell according to the invention prior to, concomitantly with or subsequently to the adenoviral sequences placed under the control of the tet O sequences or, as mentioned above, it may be added to the culture medium. It is also possible to envisage expressing the inducer (for example tTA) in the complementation cell, and adding the repressor (for example tetracycline) to the culture medium when the expression of the adenoviral genes is no longer desired.

By way of preferred examples, the adenoviral region other the E1 region consists of:

(i) all or part of the E4 region, and in particular the sequences coding for open reading frames 6 and 7 (ORFs 6/7) of the latter, or alternatively (ii) all or part of the E2 region, and in particular the sequences coding for the DBP protein (DNA binding protein) or a temperature-sensitive mutant of the latter.

Naturally, a complementation cell according to the invention can, in addition, comprise a third adenoviral region whose expression is placed under the control of the appropriate elements. In this connection, a preferred cell is intended for the complementation of an adenoviral vector which is defective for the collective early functions which are essential for replication, and comprises all or part of the E1, E2 and E4 regions, one or other or both of the latter two regions being placed under the control of a promoter equipped with regulatory sequence(s) as defined above.

One of the advantages of a complementation cell according to the invention is that it permits the production at high titer of infectious viral particles from a conventional viral vector or viral vector according to the invention. The viral titer of the final preparation (after purification) is advantageously greater than $5 \times 10^8$ pfu/ml, preferably greater than $1 \times 10^9$ pfu/ml, as an absolute preference greater than $5 \times 10^9$ pfu/ml and, as yet a further preference, greater than $5 \times 10^{10}$ pfu/ml. The term pfu is understood to refer to a particle capable of forming a plaque by infection of permissive cells. The techniques for evaluating the number of pfu are conventional and known to a person skilled in the art. The agar technique (Graham and Prevec, 1991, supra) may be mentioned. Generally, the viral titer in pfu/ml is equal to or less than the actual number of infectious viral particles capable of carrying out their gene transfer function. In effect, a certain percentage is incapable of propagating effectively and hence of generating lytic plaques on permissive cells. The titer of infectious viral particles produced by a complementation cell according to the invention is advantageously greater than $5 \times 10^9$ ifu/ml, preferably greater than $1 \times 10^{10}$ ifu/ml, as an absolute preference greater than $5 \times 10^{10}$ ifu/m [sic] and, as yet a further preference, greater than $5 \times 10^{11}$ ifu/ml. The term ifu is understood to refer to an infectious particle capable of infecting a nonpermissive target cell and of transferring its genome and permitting the expression of the genes carried by the latter. The number of ifu is estimated by the number of target cells expressing the gene of interest or a viral gene. A person skilled in the art is aware of the techniques to be employed for detecting their expression: by immunofluorescence, western blotting or alternatively staining, etc. For example, when the gene of interest consists of the LacZ gene, the protein β-galactosidase may be visualized by staining with X-Gal (5-bromo-4-chloro-3-indolyl β-D-galactopyranoside) and the number of blue cells is counted. When the CFTR therapeutic gene is employed, the expression product may be visualized by western blotting. It is also possible to look for cells expressing the adenoviral DBP, penton or fiber proteins using specific antibodies.

A complementation cell according to the invention may be generated from various cell lines by transfection of suitable portions of the adenoviral genome and a DNA fragment coding for a regulator. Among the lines which can be envisaged, there may be mentioned the Vero kidney (monkey), BHK (hamster), MDCK (dog) and MBDK (bovine) lines, the CHO line (hamster) or alternatively the human lines (HeLa, A549, MRC5, W138, etc.) available in collections such as the ATCC (Rockville, USA). However, an especially suitable cell is line 293. The use of primary lines such as primary human retina cells may also be envisaged.

An infectious viral particle according to the invention may be prepared according to any conventional technique in the field of the art (Graham and Prevect, 1991, supra), for example by cotransfection of a vector and an adenoviral fragment into a suitable cell, or alternatively by means of a helper virus supplying in trans the nonfunctional viral functions. It is also possible to envisage generating the viral vector in vitro in *Escherichia coli* (*E. coli*) by ligation or alternatively homologous recombination (see, for example, French Application 94/14470).

The invention also relates to a method of preparation of an infectious viral particle comprising a viral vector according to the invention, according to which:

(i) said viral vector is introduced into a complementation cell capable of complementing in trans said vector, so as to obtain a transfected complementation cell, (ii) said transfected complementation cell is cultured under suitable conditions to permit the expression of the viral genes and the production of said infectious viral particle, and (iii) said infectious viral particle is recovered in the cell culture.

Naturally, the infectious viral particle may be recovered from the culture supernatant, but also from the cells. According to an advantageous embodiment, an adenoviral vector and a complementation cell according to the invention are employed. According to another variant, use may be made of a conventional complementation cell. It may be necessary to add an inducer to the culture medium in the case where the expression unit comprises activable regulatory sequences. The amount to be used depends on the actual nature of the inducer. A person skilled in the art will quite obviously be able to adapt the optimal concentration in accordance with the specific data.

The invention also relates to a method of preparation of an infectious viral particle comprising a conventional viral vector, employing a complementation cell according to the invention. By way of example, the introduction of a viral vector which is defective for the E1 and E4 functions (E1-E4-) into a 293 cell expressing (i) ORFs 6/7 of the E4 region under the control of a minimal promoter equipped at its 5' end with 7 tet O sequences, and (ii) the transactivator tTA directed by the same promoter, will enable viral particles to be generated which are deficient for replication but infectious with respect to a host cell.

The subject of the invention is also a pharmaceutical composition comprising as therapeutic or prophylactic agent a viral vector, an infectious viral particle, a complementation cell or a eukaryotic host cell according to the invention, in combination with a vehicle which is acceptable from a pharmaceutical standpoint. The composition according to the invention is intended especially for the preventive or curative treatment of disorders such as:

genetic disorders (hemophilia, cystic fibrosis, diabetes or myopathy, Duchêne's [sic] myopathy and Becker's myopathy, etc.), cancers, such as those induced by oncogenes or viruses, viral diseases such as hepatitis B or C and AIDS (acquired immunodeficiency syndrome resulting from infection with HIV), and recurrent viral diseases such as the viral infections caused by herpesvirus.

A pharmaceutical composition according to the invention may be manufactured in a conventional manner. In particular, a therapeutically effective amount of a therapeutic or prophylactic agent is combined with a vehicle such as a diluent. A composition according to the invention may be administered locally, systemically or by aerosol, especially via the intragastric, subcutaneous, intracardiac, intramuscular, intravenous, intraperitoneal, intratumoral, intrapulmonary, intranasal or endotracheal route. The administration may take place in a single dose or a dose repeated one or several times after a certain time interval. The appropriate administration route and dosage vary in accordance with various parameters, for example with the individual or the disorder to be treated or alternatively with the gene(s) of interest to be transferred. In particular, the viral particles according to the invention may be formulated in the form of doses of between $10^4$ and $10^{14}$ pfu (plaque forming units), advantageously $10^5$ and $10^{13}$ pfu and preferably $10^6$ and $10^{11}$ pfu. The formulation can also include an adjuvant or an excipient which is acceptable from a pharmaceutical standpoint.

Lastly, the present invention relates to the therapeutic or prophylactic use of a viral vector, of an infectious viral particle, of a complementation cell or of a eukaryotic host cell according to the invention, for the preparation of a medicinal product intended for the treatment of the human or animal body, and preferably by gene therapy. According to a first possibility, the medicinal product may be administered directly in vivo (for example by intravenous injection, in an accessible tumor, in the lungs by aerosol, etc.). It is also possible to adopt the ex vivo approach, which consists in removing cells from the patient (bone marrow stem cells, peripheral blood lymphocytes, muscle cells, etc.), transfecting or infecting them in vitro according to the techniques of the art and readministering them to the patient. In the case where the expression unit comprises regulator sequences that respond to a repressor, it is possible to envisage administering the repressor in order to block or limit the expression of the viral genes (prior, concomitant or subsequent administration of the repressor or coexpression via conventional vectors).

The invention also extends to a method of treatment, according to which a therapeutically effective amount of a viral vector, of a viral particle, of a eukaryotic host cell or of a complementation cell according to the invention is administered to a patient requiring such treatment.

The present invention is described more fully by reference to the figures which follow and by means of the examples which follow.

EXAMPLES

Figure 1:
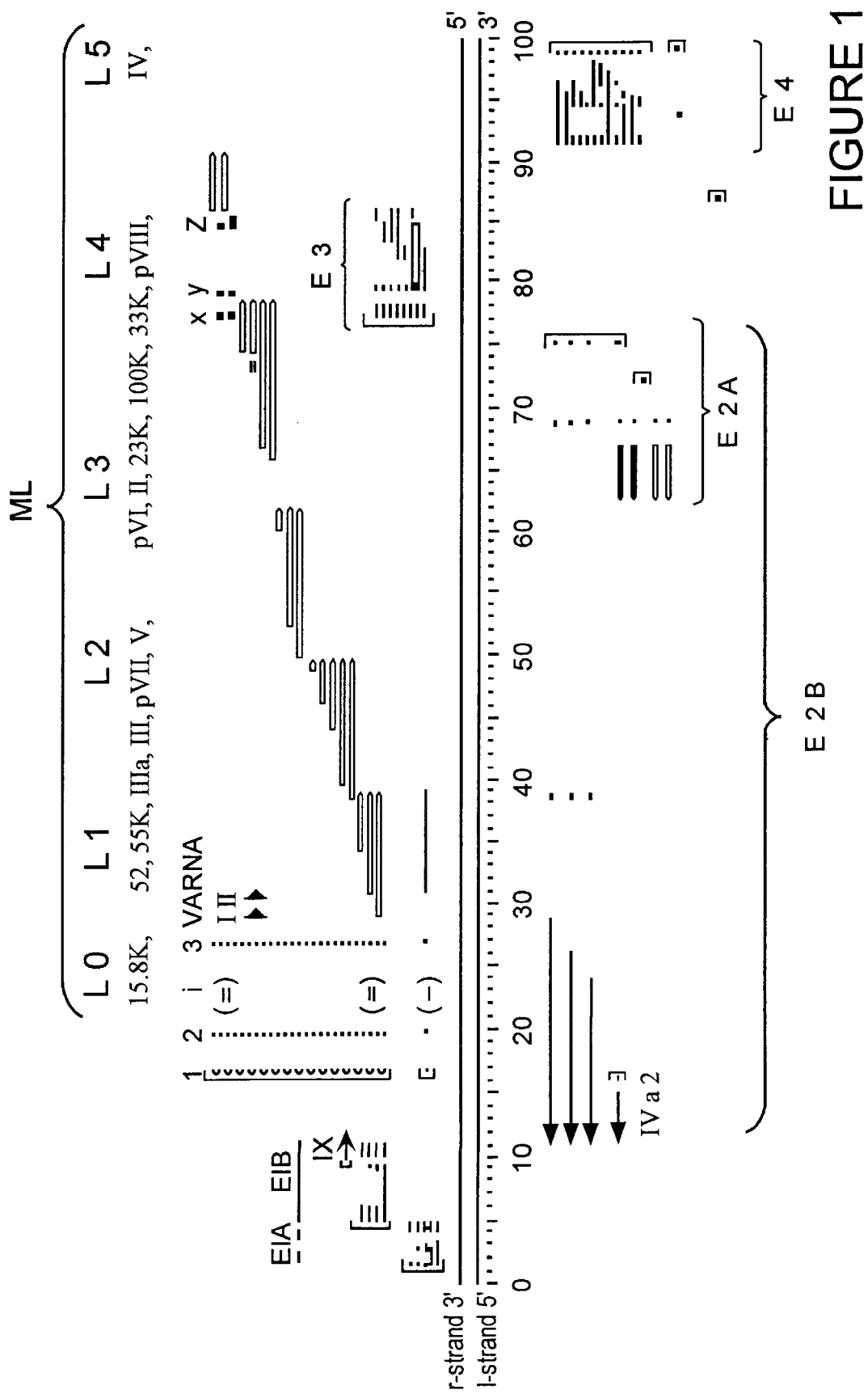
FIG. 1 is a diagrammatic representation of the genome of the human adenovirus type 5 (represented in arbitrary units from 0 to 100), showing the location of the different genes.

The examples which follow illustrate just one embodiment of the present invention.

The constructions described below are carried out according to the general techniques of genetic engineering and molecular cloning detailed in Maniatis et al., (1989, Laboratory Manual, Cold Spring Harbor, Laboratory Press, Cold Spring Harbor, N.Y.) or according to the manufacture's recommendations when a commercial kit is used. Cloning steps employing bacterial plasmids are carried out in *E. coli* strain 5K (Hubacek and Glover, 1970, J. Mol. Biol. 50, 111–127) or BJ 5183 (Hanahan, 1983, J. Mol. Biol. 166, 557–580). The latter strain is preferentially used for the homologous recombination steps. The PCR amplification techniques are known to a person skilled in the art (see, for example, PCR Protocols-A guide to methods and applications, 1990, edited by Innis, Gelfand, Sninksy and White, Academic Press Inc). As regards the repair of restriction sites, the technique employed consists of filling in the 5' protruding ends using the large fragment of *E. coli* DNA polymerase I (Klenow).

As regards the cell biology, the cells are transfected according to the standard techniques well known to a person skilled in the art. The calcium phosphate technique (Maniatis et al., supra) may be mentioned, but any other protocol may also be employed, such as the DEAE-dextran technique, electroporation, methods based on osmotic shock, microinjection or methods based on the use of liposomes. The culture conditions are, for their part, conventional.

In the examples which follow, the following cell lines are employed:

Line 293 derived from human embryonic kidney (Graham et al., 1977, supra), which results from the integration in its chromosomes of the 5' end of the Ad5 genome (5'ITR, encapsidation sequence and E1 region) (available at the ATCC under the reference CRL 1573).

Line TG1653 (described in International Application WO94/28152, Example 8), which is derived from line 293 stably transformed by the plasmid pTG1653 carrying the Ad5 E4 region (nt 32800 to 35826) and the cassette for the expression of the pac selectable gene.

It should be understood that other cell lines may be used.

Moreover, the adenoviral genome fragments employed in the different constructions described below are indicated precisely according to their position in the nucleotide sequence of the Ad5 genome as disclosed in the Genebank databank under the reference M73260.

Example 1

Complementation Line Expressing an Inducer Capable of Activating the Expression of Adenoviral Genes This example describes the construction of (1) a complementation line derived from line 293 and capable of expressing constitutively the transactivating protein tTA, and (2) an adenoviral vector in which some viral genes of the E4 region have been placed under the control of tet O sequences responding to tTa. The transfection of the vector into the line is followed by the formation of viral particles, since the E1 and E4 functions are transcomplemented by the supply of the expression products of the adenoviral E1 region and the tTa. In infected host cells which do not naturally produce the chimeric tTA protein, the expression of E4 and consequently of the late proteins (E4-dependent expression) will be considerably reduced, thereby limiting the problems of cellular immunity and inflammation.

1. Construction of a Complementation Line Expressing the Transactivator tTA

The vector pTG6529, permitting the selection of the transformed cells with puromycin, is constructed first. The vector results from the cloning into a p polyIII-I* (Lathe et al., 1987, Gene 57, 193–201) of an expression cassette composed of the SV40 promoter and the pac gene followed by the SV40 virus polyA signal. Such a construction is within the capacity of a person skilled in the art, from the corresponding sequences described in the literature (Morgenstern and Land, 1990, Nucleic Acid Res. 18, 3587–3596; Genebank reference J02400).

Figure 2:
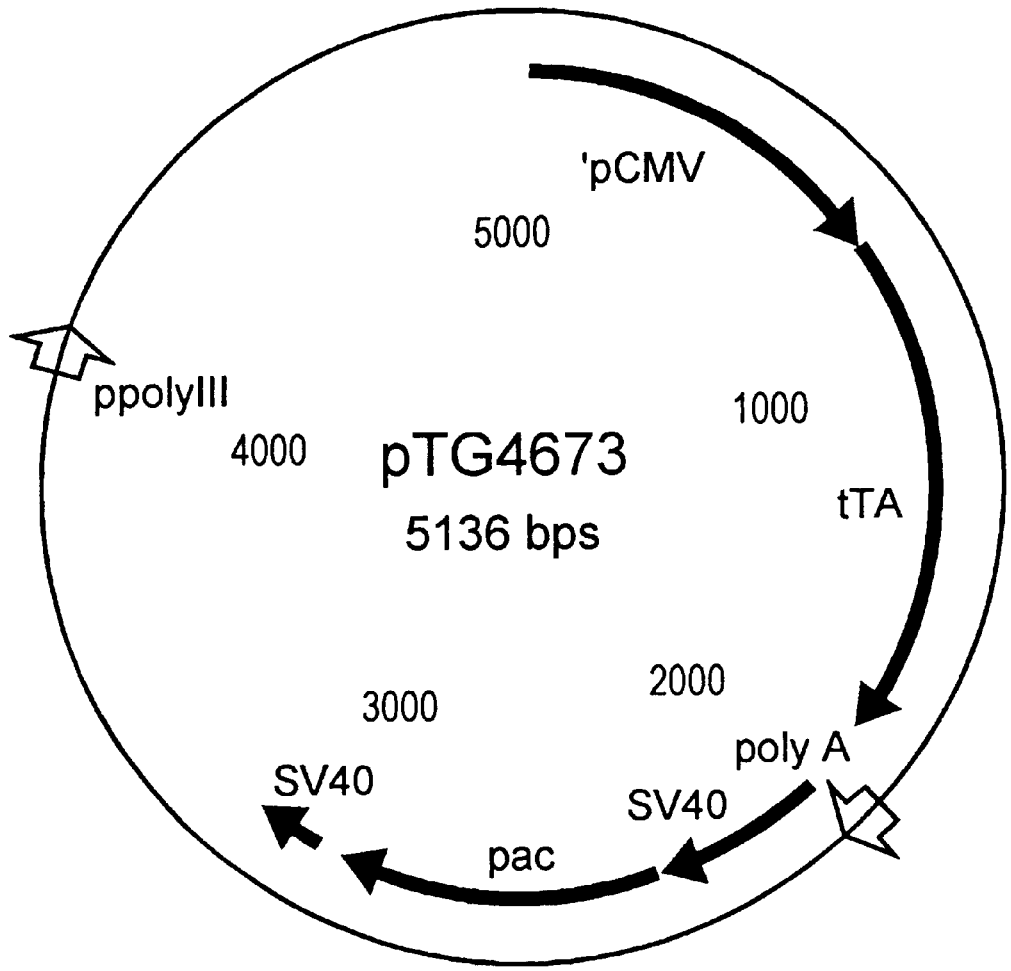
FIG. 2 is a diagrammatic representation of the vector pTG4673, permitting the constitutive expression of tTA directed by the CMV promoter (pCMV) and of the pac (puromycin resistance) selectable gene under the control of the SV40 promoter.

In parallel, the vector pUHD15-1 (Gossen and Bujard, 1992, supra) is digested with the enzymes SspI and HpaI. The fragment containing the sequences coding for tTa preceded by the CMV promoter is cloned between the same sites of pTG6529 to give pTG4673 (FIG. 2).

The vector pTG4673 is transfected in a conventional manner into 293 cells. Naturally, it would also have been possible to transfect a vector for the expression of tTA and a selectable vector (for example puHD15-1 and pTG6529). After transfection, the cells are cultured in selective medium (1 µg/ml of puromycin). 80 resistant clones were isolated and, among these, 35 tested for their capacity to transactivate a marker gene whose expression is controlled by the tet O sequences. For reasons of simplicity of implementation and of sensitivity of assay, the choice fell on the luciferase gene.

The reporter vector pUHC13-3 (Gossen and Bujard, 1992, supra) is used, in which the sequences coding for luciferase are placed under the control of the CMV minimal promoter preceded by 7 copies of tet O. The test is performed by transient transfection into the clones to be tested. Two days later, the luciferase activity is evaluated on the cell extracts employing a kit marketed by Promega ("Luciferase Assay System") and, for the measurement of the samples, a scintillation counter (LS 50000 TD, Beckman). The assay proves positive for 10 of the clones evaluated, indicating that they produce a functional tTA product capable of recognizing the tet O sequences and of activating the expression of the genes placed under their control.

2. Construction of an Adenovirus in which the Expression of the E4 Genes is Inducible with tTa.

As mentioned above, the expression of the genes coding for ORFs 6 and 7 of the E4 region is sufficient to effect viral replication without the need for complementation. This example describes the construction of an adenoviral vector from which the E1 and E3 regions and a portion of E4 have been deleted, with the exception of the sequences coding for ORFs 6 and 7 whose expression is placed under the control of tet O and, as a result, stimulated in the presence of tTA.

The vector pUHD10-3 originates from the cloning into plasmid pBR322 of an XhoI-EcoRI fragment carrying 7 tet O copies and the CMV minimal promoter (position −53 relative to the transcription startsite; see Gossen and Bujard, 1992, supra). After digestion with BamHI (site located downstream of the promoter region), the BglII-BamHI fragment obtained from pTG1653 and carrying the sequences coding for ORFs 6 and 7 is inserted to give pTG4658.

The vector pTG4664 results from the cloning of the KpnI-HpaI adenoviral fragment (nucleotides 25 838 to 32 004) between the KpnI-SmaI sites of a p poly II (Lathe et al., 1987, supra) in which the BglII site had been abolished beforehand. A large portion of E3 (nucleotides 27 871 to 30 748) is then deleted by enzymatic digestion (HpaI-HindIII).

Figure 3:
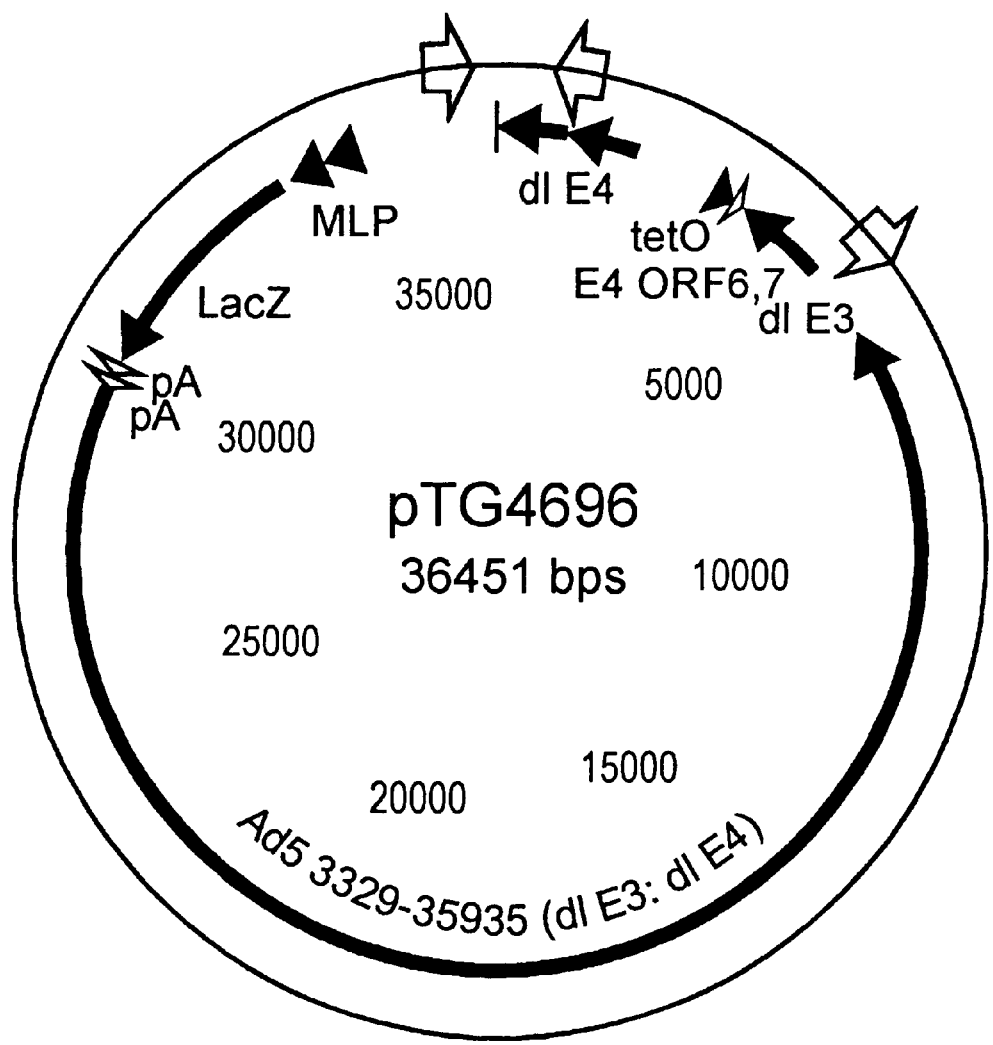
FIG. 3 is a diagrammatic representation of the adenoviral vector pTG4696 containing a cassette for the expression of ORFs 6 and 7 of the E4 region, activable by tTA.

The XhoI-HpaI fragment carrying the cassette for the regulated expression of ORFs 6 and 7 is isolated from pTG4656 and inserted after the action of the Klenow fragment into the vector pTG4664 digested with BglII and treated with the Klenow fragment, to give pTG4668 and pTG4669 according to the orientation of the cassette. The latter is introduced into an adenoviral vector by homologous recombination. The recombinant vector pTG4663, which is derived from a second generation vector (from which the E1 and E4 regions essential for replication and the nonessential E3 region have been deleted (deletion of nucleotides 27 871 to 30 748); described in Example 4 of International Application WO94/28152), into which the "MLP promoter-LacZ gene SV40 pA" expression cassette has been cloned in place of the E1 region, is used for this purpose. *E. coli* cells are cotransformed with pTG4668 or pTG4669 cleaved with HindIII and the viral vector pTG4663 linearized with SpeI to generate pTG4696 (FIG. 3) and pTG4697.

Other adenoviral vectors of similar type can be generated. It is possible, for example, to envisage placing the genes of the E2 region under the control of the tet O sequences. A person skilled in the art is familiar with the molecular biology techniques which enable the E2 promoter to be replaced by a regulable promoter such as the one isolated from the vector pUHD10-3, or the sequences upstream of the TATA box of the E2 promoter to be removed and one or more copies (preferably 7) of tet O sequences to be introduced in their place. It is also possible to construct vectors regulated at several levels, for example by insertion of tet O upstream of the TATA box of the promoters directing the expression of the viral genes of E2, E4 and/or MLP.

3. Generation of Viral Particles.

The viral vector pTG4696 or pTG4697 is transfected into one of the 10 clones producing tTA of Example 1. The cells are capable of complementing the E1 function and of producing tTa activating the expression of ORFs 6 and 7, which permits the formation of viral particles. A stock is built up which then enables the target cells to be infected at a particular m.o.i. (multiplicity of infection) capable of varying from 0.1 to 100.

Example 2

Construction of the Complementation Line 4677 for the E1 and E4 Functions, the Expression of E4 Being Inducible with tTA.

This example relates to a complementation line generated by transfection of 293 cells with a vector for the expression of ORFs 6 and 7 of E4 placed under the control of a minimal promoter preceded by 7 copies of tet O. The transfected cells are capable of complementing the E1 functions constitutively and the E4 functions inducibly with tTa. The latter may be carried by a defective adenoviral vector or a conventional expression vector.

1. Construction of the Complementation Line.

The XhoI-BamHI fragment of pTG4658 (carrying the "tet O-CMV minimal promoter-ORFs 6 and 7" cassette) is inserted between the SalI and BglII sites of the selection vector pTG6529 to give pTG4677. 60 resistant clones were generated after transfection into line 293 and selection with puromycin. The clones displaying an optimal capacity for complementation may be determined in different ways.

A first method consists in transfecting transiently the plasmid pUHD15-1 constitutively expressing tTA. Western blot analysis of cell extracts using suitable antibodies will enable the amount of ORFs 6 and/or 7 polypeptides produced in these clones, and hence their capacity for transcomplementing the E4 adenoviral function, to be evaluated. According to another method, a defective adenovirus expressing tTA may be employed. This method is detailed below.

2. Construction of a Defective Adenovirus Constitutively Expressing tTA.

Two series of constructions were carried out. pTG4682 corresponding to the adenoviral genome from which the bulk of the E1 and E3 regions has been deleted, and containing a cassette for the constitutive expression of tTA (CMV promoter) in place of the E1 region. [sic] In addition, the E4 region is deleted from pTG4683.

Figure 4:
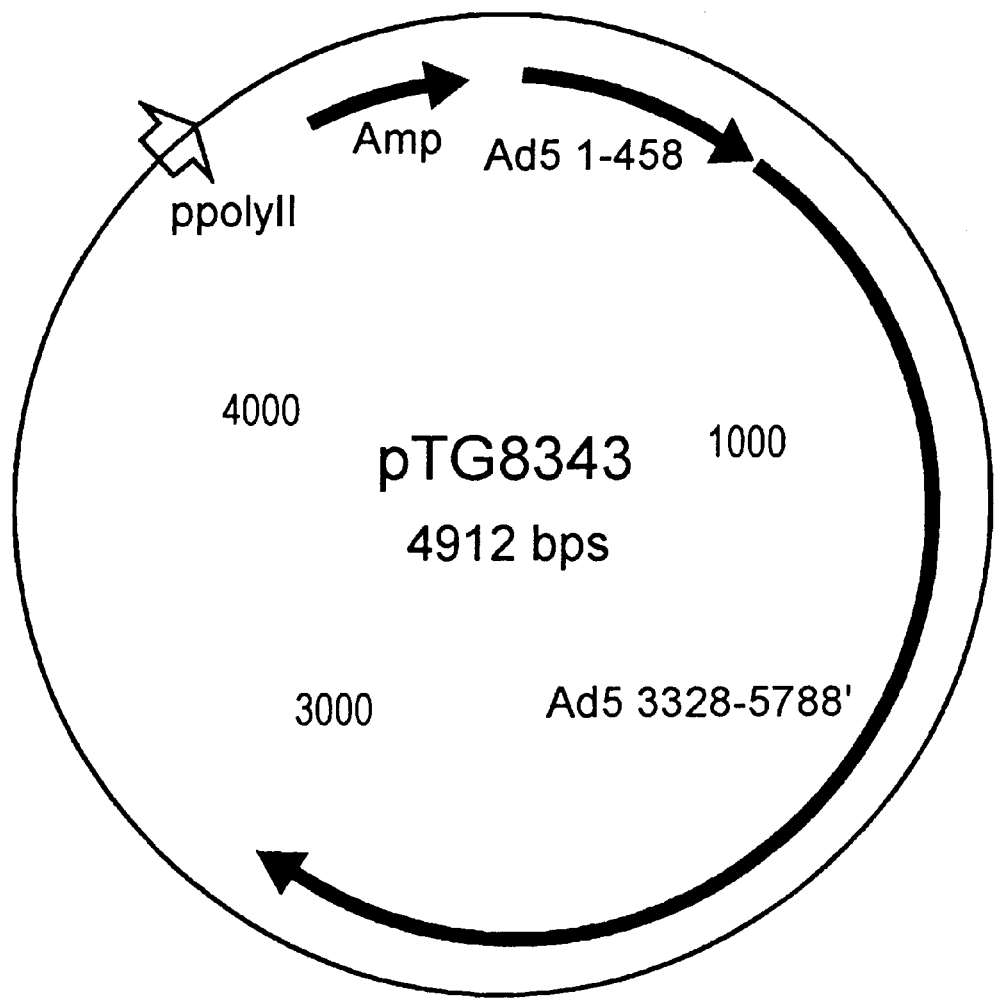
FIG. 4 is a diagrammatic representation of the vector pTG8343 containing a portion of the 5' end of the adenovirus 5 genome.
Figure 5:
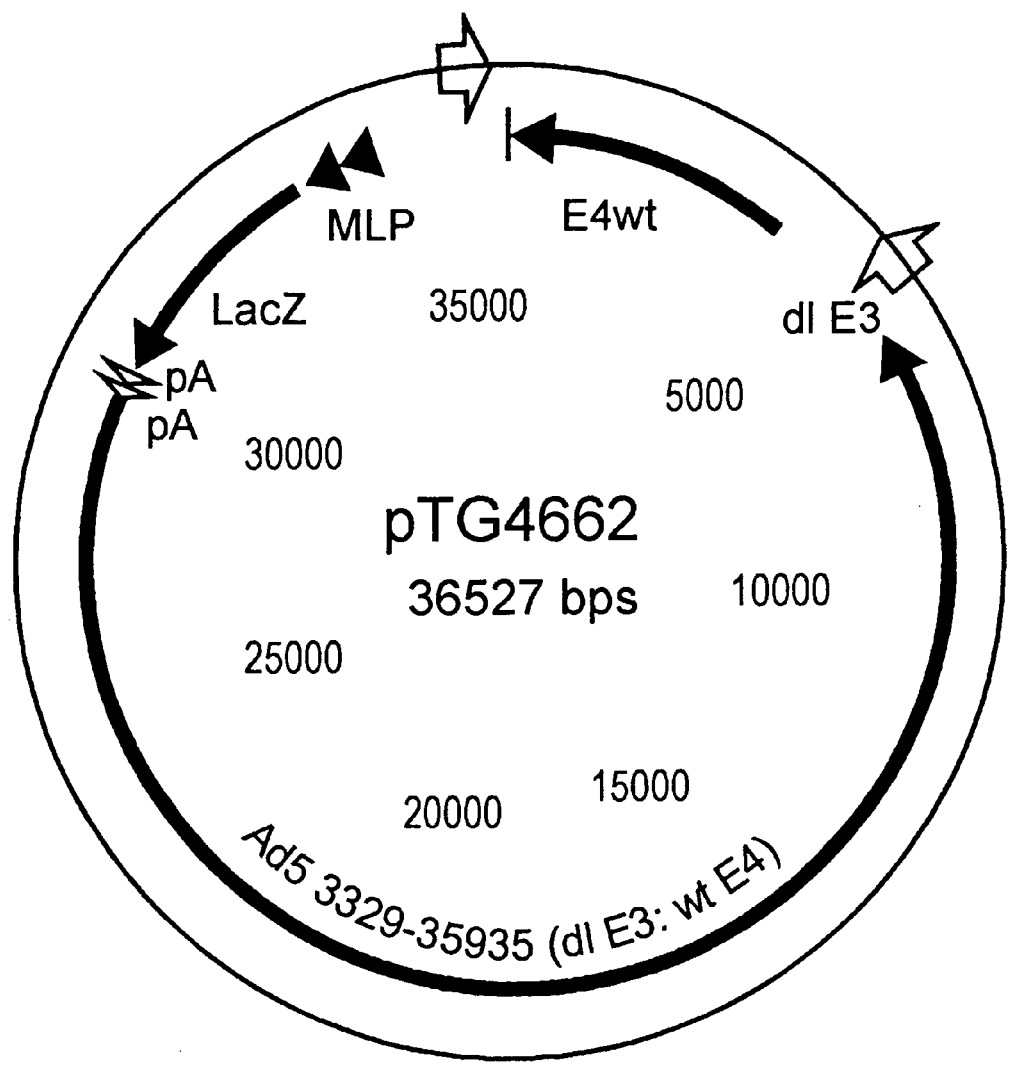
FIG. 5 is a diagrammatic representation of the vector pTG4662, a first generation recombinant adenoviral vector from which the bulk of the E1 and E3 regions has been deleted. The recombinant cassette consists of the adenoviral MLP promoter (Ad2), followed by the bacterial LacZ gene coding for β-galactosidase and the SV40 virus polyadenylation signal (pA).

The starting material is the vector pTG8343, which originates from the insertion into p poly II (Lathe et al., 1987, supra) of a portion of the 5' end of the adenoviral genome, namely the sequences extending from nucleotides 1 to 458 and 3328 to 5788 (FIG. 4). After digestion of pTG8343 with BglII and treatment with the Klenow fragment, the vector is ligated with the SspI-HpaI fragment of pUHD15-1 carrying the CMV promoter followed by the tTA sequences. pTG4674 is obtained, intended to permit the insertion of the tTA cassette by homologous recombination with an adenoviral vector comprising homologous sequences. For this purpose, the vector pTG4662 (FIG. 5) is chosen, which contains the 5' ITR and the encapsidation sequences of Ad5 (nt 1 to 458), a cassette for the expression of the LacZ gene in place of the E1 region and the remaining adenoviral sequences from the E3 region has been deleted (nucleotides 3329 to 27870 and 30749 to 35935).

Figure 6:
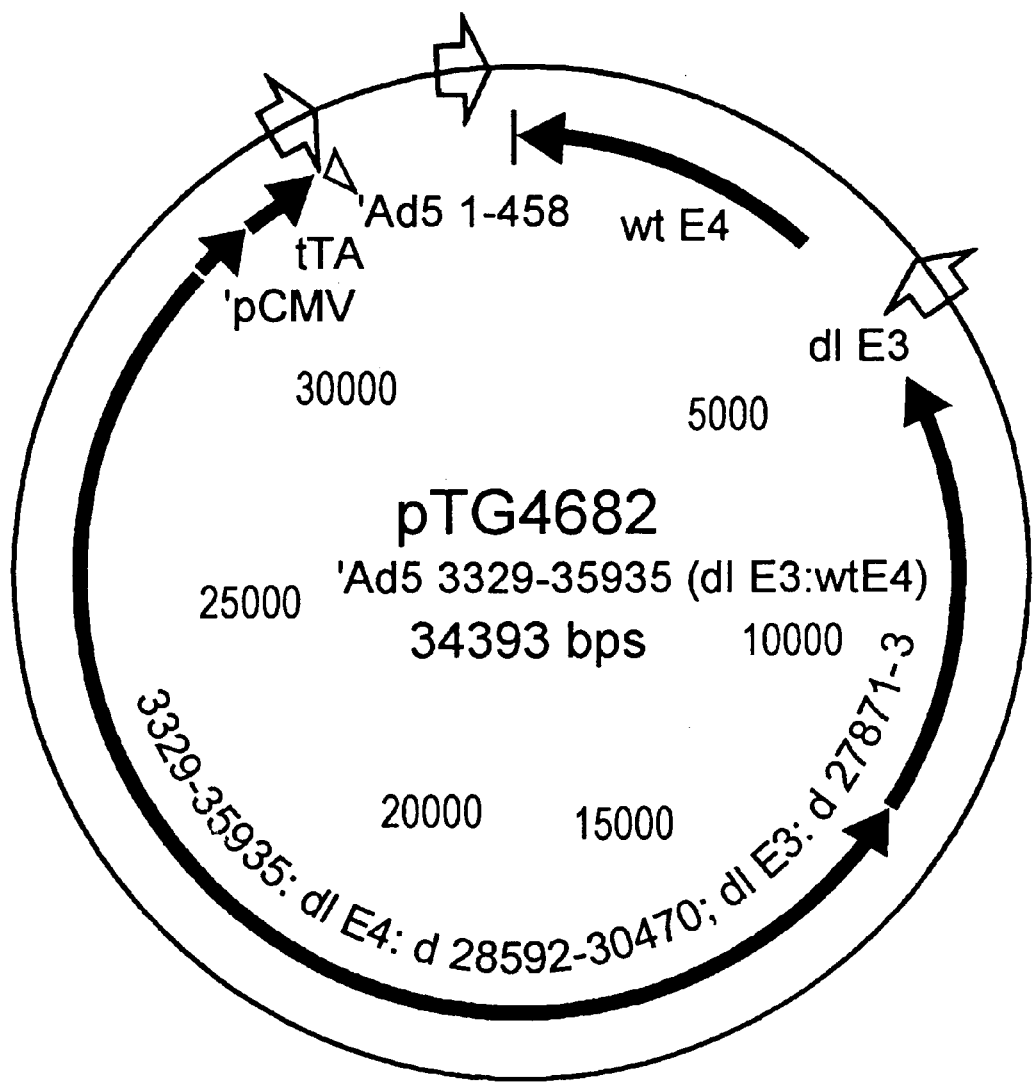
FIG. 6 is a diagrammatic representation of the vector pTG4682, an adenoviral vector from which the bulk of the E1 and E3 regions has been deleted and containing a cassette for the constitutive expression of tTA.

The *E. coli* strain BJ is cotransformed with the vectors pTG4662 linearized with ClaI and pTG4674 cleaved with SgrAI and BstEII to obtain pTG4682 (FIG. 6). This homologous recombination event permits an exchange of the LacZ cassette of pTG4662 for the tTA cassette carried by the fragment originating from pTG4674.

Figure 7:
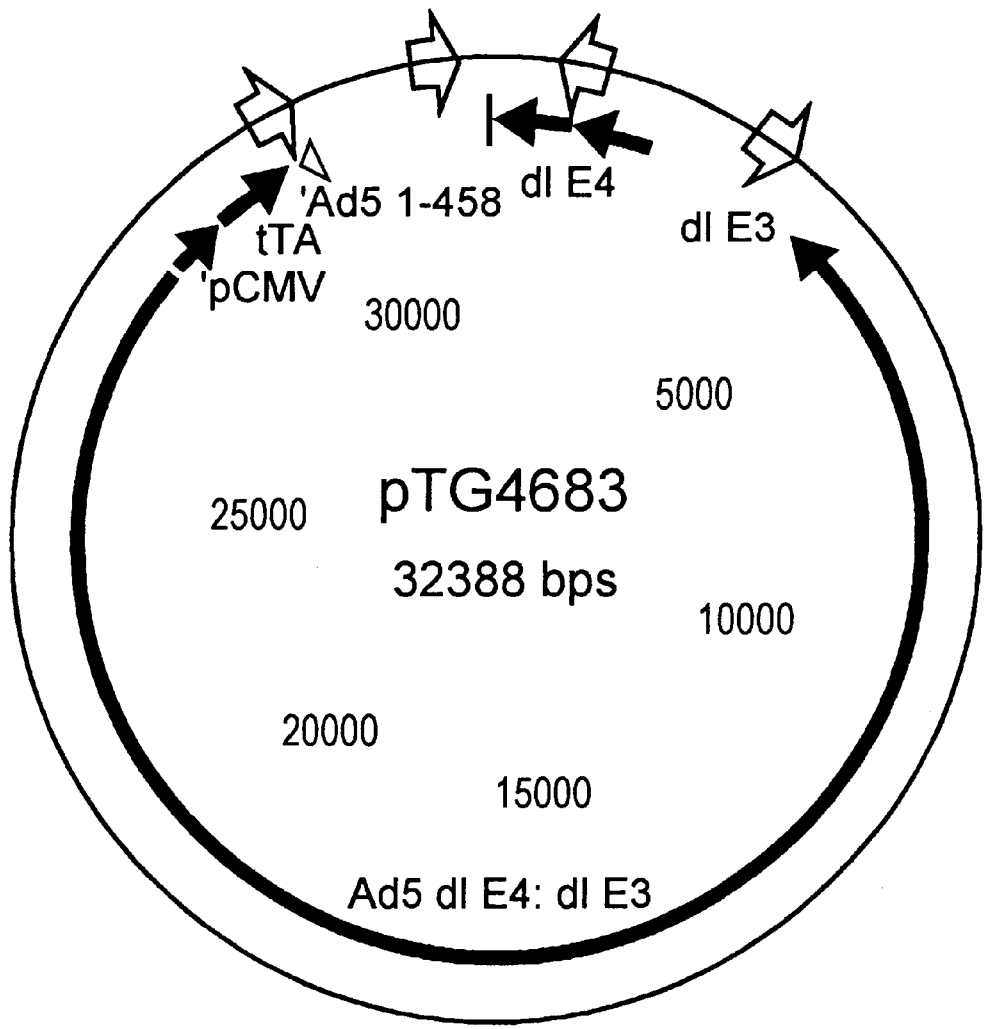
FIG. 7 is a diagrammatic representation of the vector pTG4683, an adenoviral vector from which the bulk of the E1, E3 and E4 regions has been deleted and containing a cassette for the constitutive expression of tTA.

The vector pTG4683 (FIG. 7) is obtained according to the same technology, by in vitro homologous recombination between pTG4663 cleaved with ClaI and pTG4674 digested with SgrAI and BstEII. The vector pTG4663 is similar to pTG4662, except for the fact that the bulk of the E4 region (nucleotides 32994 to 34998) has been deleted.

3. Construction of a Defective Adenovirus Inducibly Expressing tTA.

To monitor the expression of the tTA sequences, use is made of the CMV minimal promoter containing at the 5' end 7 copies of tet O sequences, which makes the system self-inducible. In effect, the production of a few tTA molecules from the uninduced promoter will enable the system to be activated. As before, two adenoviral vectors, pTG4684 and pTG4685, from which the E4 region has or has not been deleted, are generated.

Figure 8:
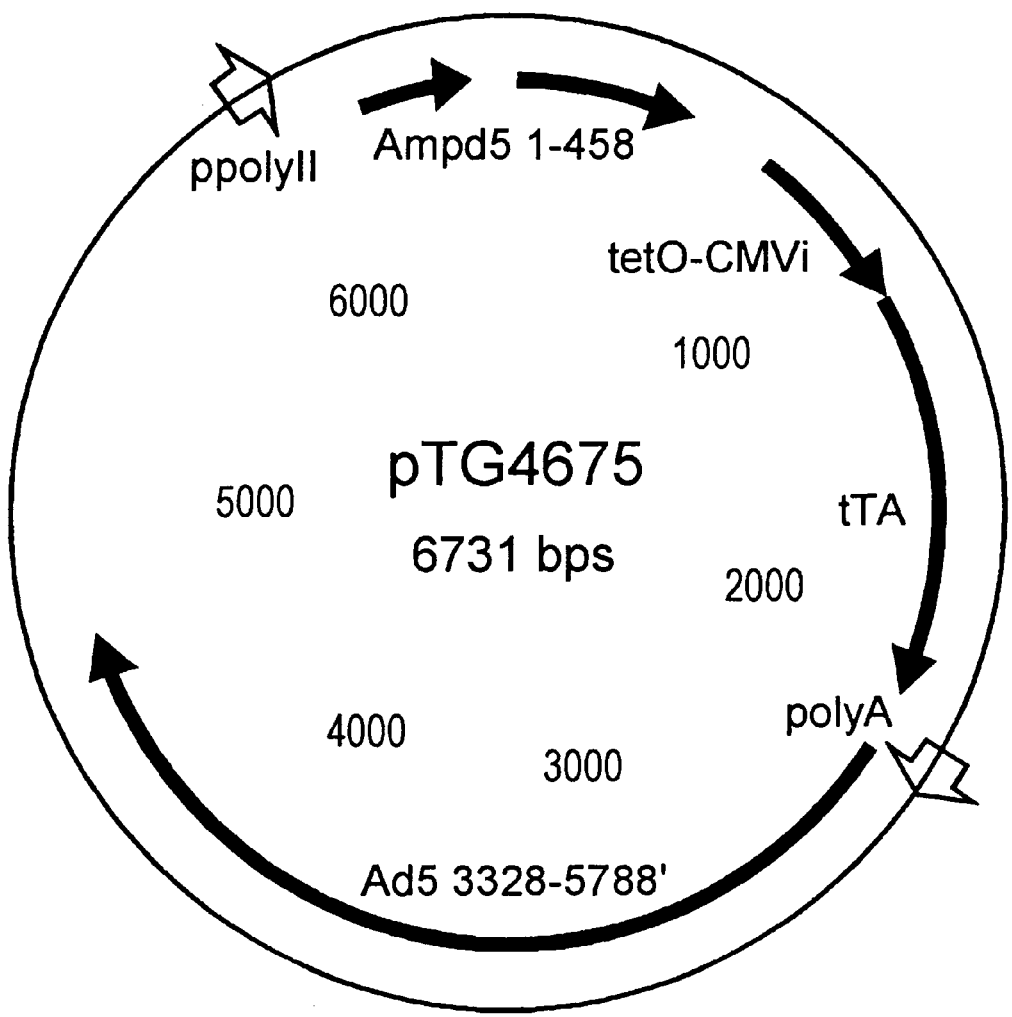
FIG. 8 is a diagrammatic representation of the vector pTG4675, permitting the inducible expression of tTA (under the control of the CMV minimal promoter (−53 to +1) preceded by 7 copies of tet O sequences, indicated on the figure by tet O-CMVi).
Figure 9:
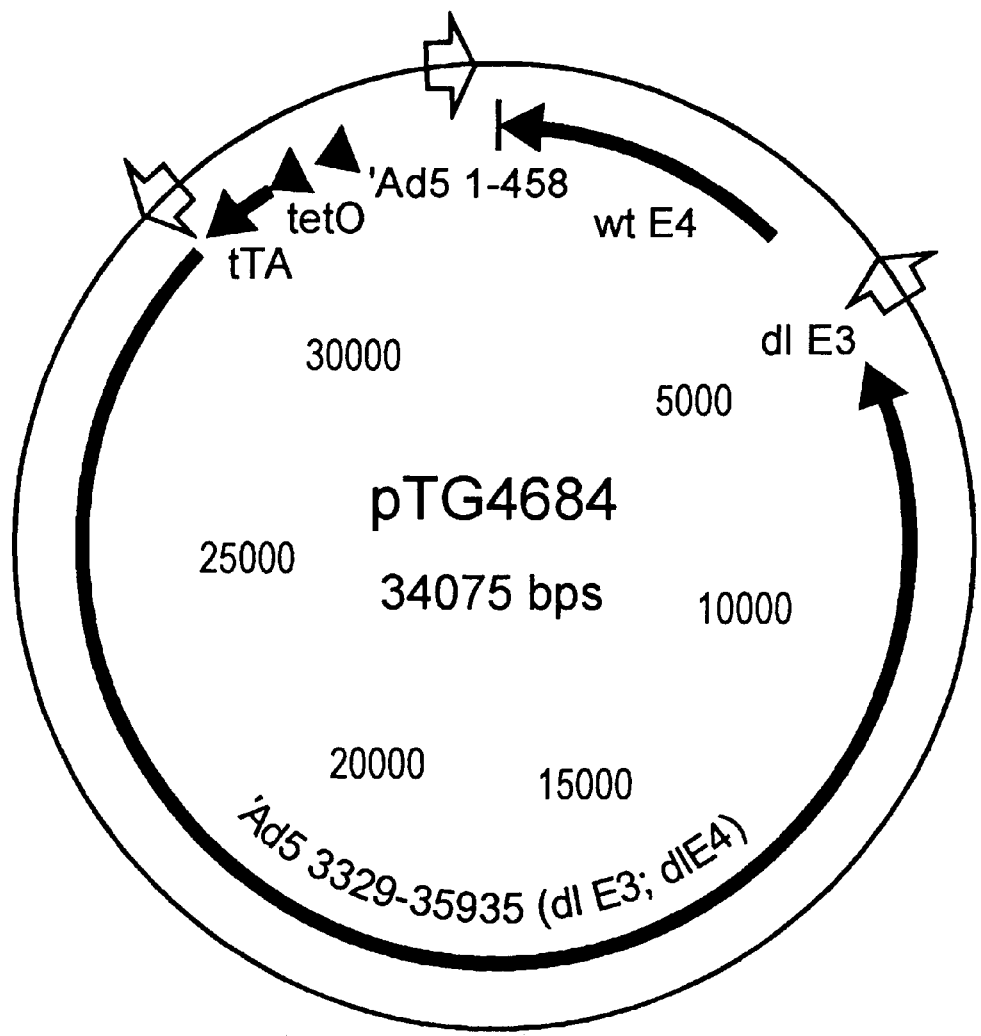
FIG. 9 is a diagrammatic representation of the vector pTG4684, an adenoviral vector from which the bulk of the E1 and E3 regions has been deleted and containing a cassette for the inducible expression of tTA.
Figure 10:
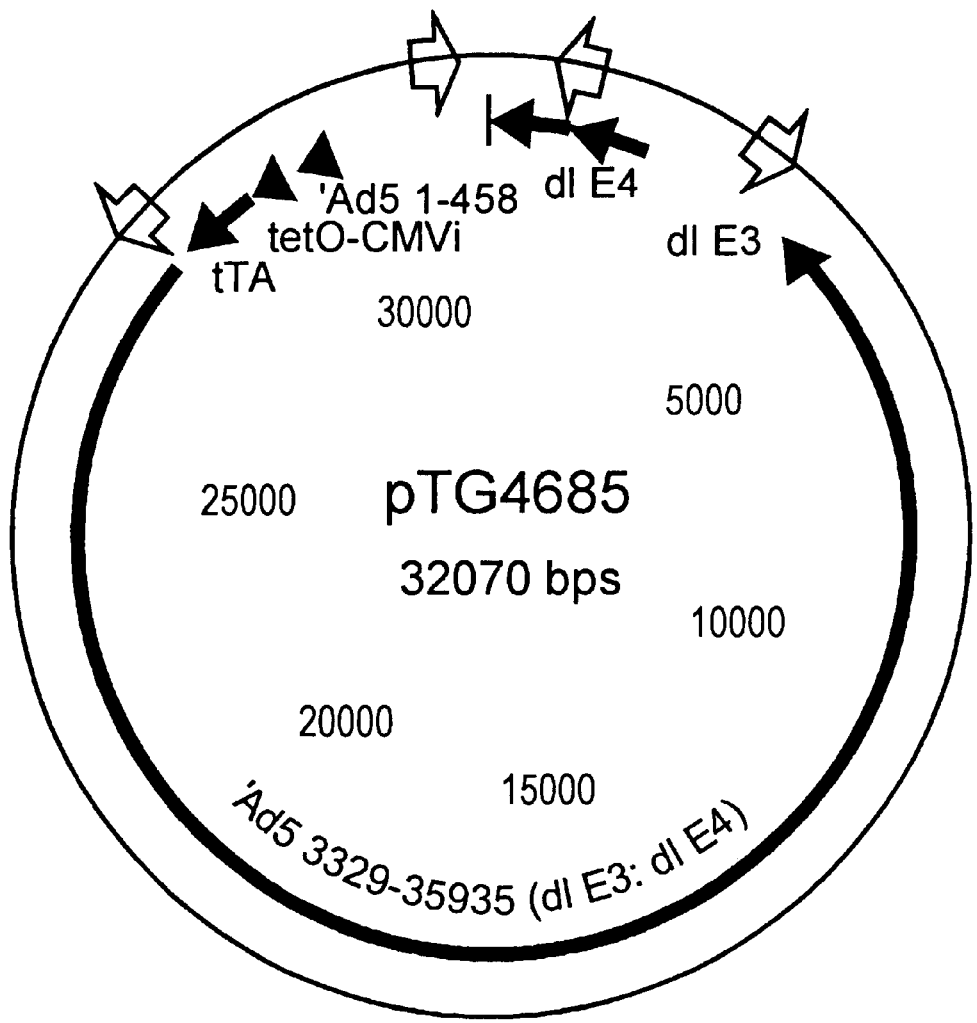
FIG. 10 is a diagrammatic representation of the vector pTG4685, an adenoviral vector from which the bulk of the E1, E3 and E4 regions has been deleted and containing a cassette for the inducible expression of tTA.

The CMV promoter of pUHD15-1 is exchanged for its regulable homolog isolated from pUHD10-3 in the form of a XhoI-EcoRI fragment. pTG4659 is obtained. The cassette is isolated from the latter by digestion with SspI and HpaI, and cloned into the vector pTG8343 linearized with BglII and treated with the Klenow fragment to give pTG4675 (FIG. 8). The *E. coli* strain BJ is then co-transformed with the above vector treated with SgrAI and BstEII and pTG4662 or pTG4663 linearized with the enzyme ClaI, so as to generate by homologous recombination the viral vectors pTG4684 (FIG. 9) and pTG4685 (FIG. 10).

The viral particles may be obtained by simple transfection of a suitable cell line such as that of Example 2.1 in the absence of tetracycline (the addition of the antibiotic to the culture medium having an inhibitory effect on the transcription of tTA and ORFs 6 and 7, which is regulated by the tet O sequences).

4. Functional Tests of Microinfection and of Microtitration.

The experiments are carried out in parallel on 293 cells complementing the E1 function and 1653 cells complementing the E1 and E4 functions. The cells are distributed in a culture plate on the basis of approximately $5 \times 10^4$ cells per well. They are then transfected with the vectors to be tested, pTG4682 to 4685. Their capacity for forming plaques in both cell types (according to their rate of appearance) is evaluated, as well as their size. As controls, the recombinant vectors pTG4662 and pTG4663 which correspond, respectively, to first generation adenoviral vectors (deletion of E1 and E3) and second generation adenoviral vectors (additional deletion of E4), and which do not express tTA, are used.

The generation of viral particles from the construction pTG4662 is readily detectable in both cell lines (formation of large plaques appearing rapidly). pTG4663, for its part, can be propagated only in 1653 cells complementing E1 and E4, and gives small plaques which appear late.

As regards the vectors pTG4682 and pTG4684, their transfection into 293 and 1653 cells is rapidly followed by the formation of large, readily identifiable plaques (behavior similar to the pTG4662 control). The vectors pTG4683 and pTG4685 from which the E4 region has been deleted behave comparably to pTG4663: in line 1653 the viral particles appear slowly, forming small-sized plaques, whereas in line 293 no plaques are detected. These data appear to indicate that the expression of tTA is not prejudicial to viral propagation or toxic for cell growth.

As mentioned above, this technology may be applied to the line of Example 1 (293/pTG4673) and vectors pTG4696 and pTG4697.

Example 3

Construction of the Complementation Line 5606 for the E1 and E4 Functions, in which the Expression of E4 is Inducible with the tTA Produced by the Line.

This example describes a complementation cell line permitting the propagation of E1− and E4− deficient adenovirus, obtained by transfection of 293 cells with the vector pTG5606 carrying, besides the pac selectable gene, the sequences coding for ORFs 6/7 and for tTA placed under the control of the promoter hereinafter designated pCMV*, corresponding to the CMV minimal promoter (position −53 relative to the transcription startsite) equipped at the 5' end with 7 consecutive tet O sequences. This self-inducible system makes possible, in the first place, the production of a few tTA molecules from the minimal CMV promoter, which will be able to act positively on the tet O sequences and amplify their own synthesis and that of the ORF6/7 products in a sufficient amount for an effective complementation of the defective vectors.

1. Construction of Plasmid pTG5606

Figure 11:
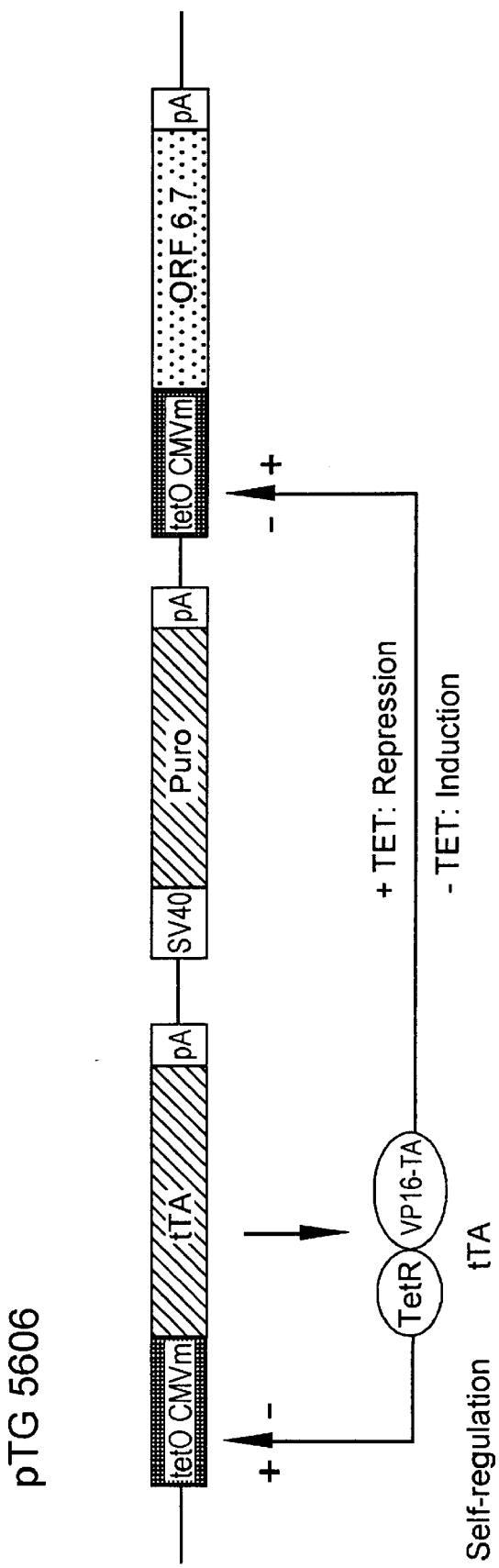
FIG. 11 is a diagrammatic representation of the vector pTG5606, permitting the expression of ORFs 6/7 of the adenoviral E4 region and of tTA under the control of the CMV minimal promoter preceded by 7 copies of tet O sequences and the pac selectable gene conferring puromycin resistance.

The first step is to construct the vector pTG4688, which results from the cloning of the cassette (CMV promoter/enhancer-tTA), purified from pTG4673 (Example 1.1) cleaved with HpaI and PvuI, into the vector pTG4677 (Example 2.1) digested with these same enzymes. The vector pTG5606 is obtained from the above vector by replacement of the CMV promoter/enhancer by the regulable promoter pCMV*. To this end, pTG4688 is linearized with the enzymes ScaI-XbaI before inserting the ScaI-XbaI fragment carrying PCMV* isolated from pTG4659. Plasmid pTG5606 thus generated (FIG. 11) comprising [sic] the following three expression cassettes:

a first cassette composed of the pCMV* promoter, the sequences coding for the tTA transactivator and the SV40 virus polyA sequences, a second cassette composed of the puromycin resistance gene (pac gene) under the control of the early promoter and the SV40 virus pA sequences, and a third cassette composed of the pCMV* promoter followed by the sequences coding for the adenovirus 5 ORFs 6/7 equipped with their own polyA signal.

2. Generation of the Complementation Line 5606.

$4 \times 10^6$ 293 cells (ATCC CRL1573) are cultured in DMEM medium (Dubelco's [sic] modified Eagle's medium) in the presence of 10% FCS. At around 70 to 80% confluence, they are distributed in several dishes and are then transfected with 10 μg or 20 μg of plasmid pTG5606 (Gibco-BRL transfection kit; ref. 530-8120SA). After 48 hours, the cells are cultured in selective medium (puromycin 0.7 μg/ml for the first week and thereafter 1 μg/ml). The resistant clones are amplified in the above selective medium, where appropriate in the presence of tetracycline. The latter exerts a repressor effect on the tet O sequences, and the object of adding it is to reduce the synthesis of the expression products of ORFs 6/7 which might prove cytotoxic and lead to cell death. Thus, three batches were constituted according to the tetracycline concentration contained in the medium, 0 μmg/ml, 1 μg/ml and 5 μg/ml, respectively. A large number of clones appear irrespective of the amounts of DNA transfected and the culture conditions.

The clones coexpressing the E1 and E4 genes were screened by a microinfection and microtitration technique. About one hundred 5606 clones are infected at a low moi (multiplicity of infection) with a E1–E4-defective adenoviral vector (see, for example, International Application WO 94/28152). A cytopathic effect is observed 48 to 72 h after infection for 10 to 16% of them, depending on the batch from which they originate. The cytopathic effect is evidence of the multiplication of the doubly defective viruses and reflects the capacity of the clone for transcomplementation. The titer of infectious viral particles is estimated by a microwell titration technique on a permissive cell. To this end, the viral particles are recovered from the infected cultures by three cycles of freezing-thawing and the viral supernatants to be titrated are diluted serially on the basis of 100 μl per well and placed in contact with $4 \times 10^4$ 1653 cells. The viral titer is evaluated crudely by observation of the cytopathic effect at the different dilutions. The most productive 5606 clones (cytopathic effect at high dilutions) are selected for a more accurate study of the yield in terms of pfu/ml and ifu/ml.

The selected 5606 clones are cultured ($5 \times 10^5$ cells) and infected again with an E1–E4-adenoviral vector. It is possible to use, for example, the vectors AdTG8595 and AdTG4651 from which the E1, E3 (nt 28592 to 30470) and E4 (nt 32994 to 34998) regions have been deleted, and comprising in place of E1 the cassette for the expression of the gene of interest, MLP-LacZ [sic] promoter and MLP-CFTR gene promoter, respectively. As before, the viral supernatants are recovered and the titer in pfu/ml is determined by infecting a permissive line (line 1653 or the 5606 productive clone) with suitable dilutions of viral superantant and counting the lytic plaques in agar. Two clones, designated #5-19/1 and #5-38, give titers varying from 1 to $5 \times 10^9$ pfu/ml (titration performed on themselves). The yield of infectious particles (ifu/ml) is evaluated by counting the infected cells expressing the gene of interest. Thus, the viral superanants obtained from the 5606 clones infected with AdTG8595 are titrated with themselves and, 48 hours after infection, the adherent cells are fixed (PBS buffer containing 2% of formaldehyde and 0.2% of glutaraldehyde) and the production of β-galactosidase visualized with the dye X-Gal (1 mg/ml in PBS buffer to which 5 mM K ferricyanide, 5 mM K ferrocyanide and 2 mM $MgCl_2$ are added). The titers obtained are between $10^{10}$ and $10^{11}$ ifu/ml.

Lastly, it is verified that the expression of the late viral genes is not impaired, which might lead to a defect of assembly of the viral particles. The production of fiber and penton is determined by western blotting on the pellets of infected cells recovered after the cycles of freezing-thawing. The analysis is performed according to standard techniques on an aliquot of cell extract corresponding to 3 μg of proteins using antibodies directed against the fiber (Henry et al., 1994, J. Virol. 68, 5239–5246) or the penton base (Boulanger et al., 1973, Eur. J. Biochem. 39, 37–42), followed by peroxidase-labelled anti-rabbit antibodies (Amersham, NA 934). Visualization takes place using the ECL detection kit (Amersham, RPN 2106). The data show that the E1–E4-adenoviruses generated from the two 5606 clones are capable of producing the late proteins at a level approaching that obtained in 293 cells infected with an E1⁻ virus.

In conclusion, the 5606 clones #5-19/1 and #5-38 constitute E1 and E4 complementation lines capable of amplifying the doubly defective vectors at a titer exceeding $1 \times 10^9$ pfu/ml, a titer compatible with a large-scale production.

Example 4

Construction of the Complementation Line 9579 for the E1 and E2A Functions, in which the Expression of E2A is Inducible with tTA, the Latter Being Produced by the Line.

This example describes a complementation cell line permitting the propagation of E1⁻ and E2A⁻ deficient adenoviruses obtained by transfection of 293 cells with the vector pTG9579 permitting a self-inducible expression of the DBP protein according to the same principle as in the previous example.

1. Construction of the Vector pTG9579

The vector pTG9579 is constructed in the following manner:

The 3' end of the adenovirus 5 genome is isolated from a preparation of genomic DNA digested with DraI-BsmBI. The corresponding fragment is subcloned into the SmaI site of the vector pUC19 (Gibco BRL) to give the intermediate vector pTG9568. The STOP codon of the DBP sequence is found to be destroyed by the cleavage with DraI. It is restored by introduction between the EcoRV and BamHI sites of pTG9568 of a fragment containing the correct sequence obtained by PCR amplification from the genomic template and the appropriate primers. pTG9571 is obtained.

Separately, the vector pUHD-10-3 is linearized with HindIII and treated with the Klenow fragment, and the cassette for the expression of the neo gene (Colbère-Garapin et al., 1981, J. Mol. Biol. 150, 1–14) directed by the early promoter and the SV40 pA signal are inserted. The vector thereby obtained, pTG9555, is linearized with XbaI and then subjected to the action of the Klenow fragment, before cloning the fragment carrying the DBP sequence isolated from pTG9571 after cleavage with XhoI and EcoRI and treatment with the Klenow fragment. Lastly, the HpaI-XhoI fragment (Klenow) isolated from pTG4659 carrying the cassette for the expression of the tTA gene is introduced into the XhoI site, treated with the Klenow fragment, of the vector pTG9577 generated in the previous step, to give pTG9579. To summarize, the latter comprises:

- a first cassette composed of the PCMV* promoter followed by the sequences coding for the tTA transactivator and the SV40 virus polyA sequences,
- a second cassette composed of the neo gene for resistance to the antibiotic G418 under the control of the early promoter and the SV40 virus pA sequences, and
- a third cassette composed of the sequences coding for the adenovirus 5 DBP protein under the control of the pCMV* promoter and the SV40 virus pA sequences.

Figure 12:
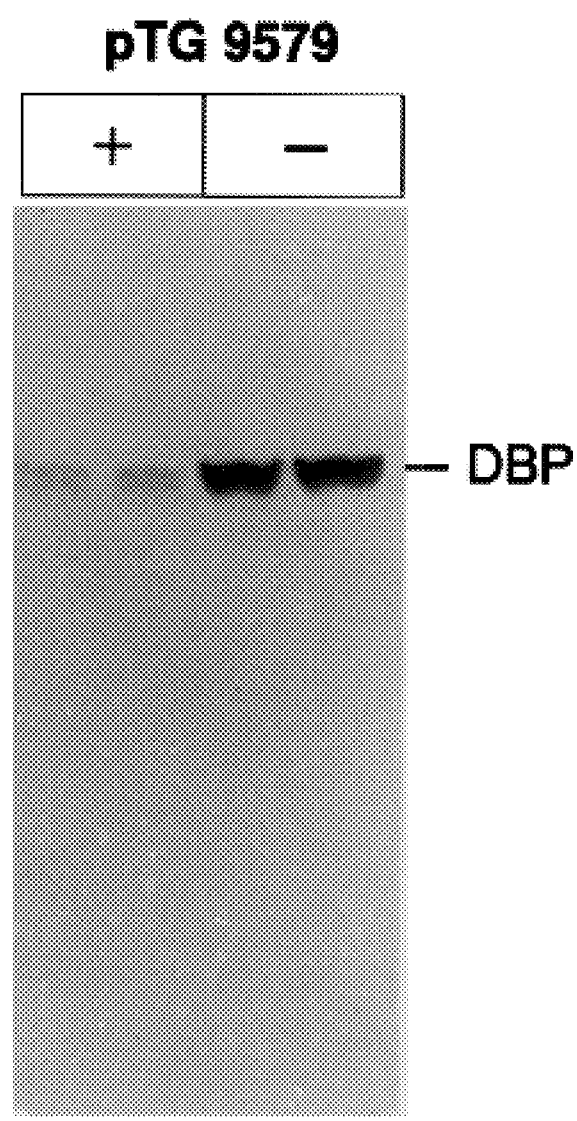
FIG. 12 is a western blot analysis of the expression of the DBP protein in 293 cells transfected transiently with the vector pTG9579 and cultured in the presence (+) and in the absence (−) of tetracycline.

The production of a functional DBP protein by pTG9579 may be verified by transient transfection into 293 cells. Briefly, $1 \times 10^6$ cells are transfected with 5 μg of vector by the calcium phosphate method and then cultured in the presence (1 μg/ml) or in the absence of tetracycline. 4 days after transfection, the cells are recovered and the cell pellet is treated with 100 μl of lysis buffer (50 mM Tris-HCL [sic], 1 mM $MgCl_2$, 1 mM EDTA, 5 mM KCl, 150 mM NaCl and 1% Triton X-100) in order to solubilize the proteins. 7 μl of protein extract are taken up in a Tris-glycine loading buffer containing 5% of β-mercaptoethanol and subjected to an 8–16% PAGE electrophoresis under denaturing conditions. After transfer onto nitrocellulose membranes, the DBP protein is visualized by western blotting using an antibody specific for the adenoviral DBP protein (Reich et al., 1983, Virology, 128, 480–484; for example the mouse monoclonal antibody α72KB 6-8) and a peroxidase-labelled sheep anti-mouse immunoglobulin antibody (Amersham; NA 931). Visualization is performed with the ECL kit (Amersham, RPN 2106). The results presented in FIG. 12 show that the DBP protein is produced in 293 cells transiently transfected with the vector pTG9579, and in a regulated manner since the expression is reduced in the presence of tetracycline.

2. Generation of the Complementation Cell Line 9579

20 μg of plasmid pTG9579 are used to transfect $3 \times 10^6$ 293 cells (Gibco BRL transfection kit; ref. 530-8120SA). The clones are selected in the presence of 600 μg/ml of G418 and 1 μg/ml of tetracycline, and tested for their capacity to produce the DBP protein by the western blotting technique described above. 20% of them express detectable amounts of the DBP, of which two, designated #7-44 and #7-32, at a level close to that obtained in line gmDBP6 in the presence of dexamethasone. The latter line constitutes the reference line for complementation of the E2A function (Brough et al., 1992, Virol. 190, 624–634). It is derived from HeLa cells transfected with an expression cassette comprising the sequences coding for DBP, directed by the dexamethasone-inducible MMTV promoter.

The DBP-positive clones are cultured and infected at an moi≧1 with the adenovirus H5dl802 which is defective for the E2A function (Rice and Klessig, 1985, J. Virol. 56, 767–778). Two days after infection, the viral supernatants are collected after lysis of the cells by consecutive cycles of freezing-thawing, diluted serially and titrated on the permissive line gmDBP6. The presence of viral particles is observed in the supernatants originating from the clones #7-44 and #7-32, showing their capacity to complement the E2A function. The same type of experiment is carried out with the vector pTG9542 (E1⁻ (LacZ) E2A⁻ and E3⁻). Infectious particles are produced, showing that these two clones are capable of propagating and amplifying doubly defective vectors. Furthermore, these particles cannot be propagated on line 293, confirming the E2A⁻ phenotype and the absence of revertants.

Amplification experiments conducted with the clone #7-44 infected with the AdTG9542 virus showed an amplification factor of approximately 125 when the titration is performed 4 days after infection.

We claim:

1. Adenoviral vector, comprising an expression unit containing one or more viral genes; said expression unit being functional in a complementation cell and nonfunctional in a host cell, and comprising one or more heterologous regulator sequence(s).

2. Adenoviral vector according to claim 1, wherein said expression unit comprises one or more regulatory sequence(s) which activate the expression of said viral gene in the presence of an inducer and/or inhibit the expression of said viral gene in the presence of a repressor.

3. Adenoviral vector according to claim 1 wherein said regulatory sequence can act at the level of transcription, elongation, transport or stability of the messenger RNAs or translation.

4. Adenoviral vector according to claim 1, wherein said expression unit comprises one or more regulatory sequence(s) selected from the group consisting of TAR, RRE, GRE, PRE, ERE and Gal4 upstream activating sequences (UAS) sequences or the regulatory sequences of the metallothionein gene or of the bacterial tryptophan lactose or tetracycline operons.

5. Adenoviral vector according to claim 1, derived from an adenovirus of human, canine, avian, bovine, murine, ovine, porcine or simian origin, or alternatively from a hybrid comprising adenoviral genome fragments of different origins.

6. Adenoviral vector according to claim 1, comprising an exogenous nucleotide sequence placed under the control of the elements needed for its expression in the host cell.

7. Infectious viral particle comprising a adenoviral vector according to one claim 1.

8. Eukaryotic host cell comprising a adenoviral vector according to claim 1.

9. A composition comprising a adenoviral vector according to claim 1 in combination with a suitable carrier.

10. Viral vector according to claim 3, wherein said regulatory sequence is placed in the promoter of said unit.

11. Adenoviral vector according to claim 10, wherein said regulatory sequence is placed upstream of a TATA box.

12. Adenoviral vector according to claim 4, wherein said expression unit comprises one or more regulatory sequence(s) from the tetracycline operon, placed upstream of the TATA box of said promoter, to give a promoter which is activable by an inducer of the tetracycline transactivator (tTA) type and repressible by tetracycline.

13. Adenoviral vector according to claim 4, wherein said expression unit comprises one or more regulatory sequence(s) from the tetracycline operon, placed downstream of the TATA box of said promoter, to give a promoter which is repressible by the tetracycline repressor (TetR).

14. Complementation cell for the complementation of an adenoviral vector which is defective for the E1 function and at least one second, late or early adenoviral function, comprising:
  (i) a first cassette for the expression of all or part of the E1 region of an adenovirus, placed under the control of the elements necessary for its expression in said complementation cell, and
  (ii) a second cassette for the expression of all or part of a late or early region of an adenovirus other than the E1 region, placed under the control of the elements necessary for its expression in said complementation cell, said elements comprising one or more regulatory sequences according to claim 4.

15. Adenoviral vector according to claim 5 wherein it is defective for replication.

16. Adenoviral vector according to claim 5 comprising one or more expression unit(s) containing one or more viral genes of the E2, E4 or L1–L5 regions.

17. Adenoviral vector according to claim 15, wherein it lacks at least all or part of the E1 region and, optionally, all or part of the E3 region.

18. Adenoviral vector according to claim 16, comprising an expression unit containing one or more regulatory sequence(s) from the tetracycline operon, placed upstream of the TATA box of the promoter and open reading frames (ORFs) 6 and 7 of the E4 region, so that the expression of said reading frames is activable by an inducer of the tetracycline transactivator (tTA) type and repressible by tetracycline.

19. Adenoviral vector according to claim 6, wherein the exogenous nucleotide sequence is selected from the group consisting of the genes coding for a cytokine, a cell or nuclear receptor, a ligand, a coagulation factor, the CFTR protein, insulin, dystrophin, a growth hormone, an enzyme, an enzyme inhibitor, a polypeptide having an antitumor effect, a polypeptide which inhibits a bacterial, parasitic or viral infection, an antibody, a toxin, an immunotoxin and a marker.

20. Method of preparation of an infectious adenoviral particle according to claim 7, comprising:
  (i) introducing a adenoviral vector according to claim 1 into a complementation cell which complements in trans said adenoviral vector, to obtain a transfected complementation cell;
  (ii) culturing said transfected complementation cell under suitable conditions to permit the expression of the adenoviral genes and the production of said infectious adenoviral particle; and
  (iii) recovering said infectious adenoviral particle in the cell culture.

21. Eukaryotic host cell comprising a infectious viral particle according to claim 7.

22. A composition comprising an infectious adenoviral particle according to claim 7 and a suitable carrier.

23. Complementation cell which complements at least one adenoviral vector function, comprising an inducer and/or a repressor.

24. Complementation cell according to claim 23, comprising a DNA fragment coding for an inducer and/or a repressor.

25. Complementation cell according to claim 23, wherein it is derived from cell line 293.

26. Complementation cell according to one of claim 23 for the complementation of an adenoviral vector which is defective for the E1 and E4 functions, wherein the second expression cassette is a cassette for the expression of all or part of the E4 region of an adenovirus.

27. Complementation cell according to claim 23 for the complementation of an adenoviral vector which is defective for the E1 and E2 functions, wherein said second expression cassette is a cassette for the expression of all or part of the E2 region of an adenovirus.

28. Complementation cell according to claim 23 for the complementation of an adenoviral vector which is defective for the E1 function and at least two other late or early adenoviral functions comprising:
   (i) a first cassette for the expression of all or part of the E1 region of an adenovirus, placed under the control of the elements necessary for its expression in said complementation cell, and
   (ii) a second cassette for the expression of all or part of a late or early region of an adenovirus other than the E1 region, placed under the control of the elements necessary for its expression in said complementation cell, said elements comprising one or more regulatory sequences according to claims 5, 6 or 7, and
   (iii) a third cassette for the expression of all or part of a late or early region of an adenovirus other than the E1 region and the adenoviral region of the second expression cassette, placed under the control of the elements necessary for its expression in said complementation cell.

29. Complementation cell according to claim 23, wherein the titer of viral particles produced by said complementation cell is greater than $5 \times 10^8$ pfu (plaque forming units)/ml.

30. Complementation cell according to claim 23, wherein the titer of viral particles produced by said complementation cell is greater than $1 \times 10^{10}$ ifu (infectious units)/ml.

31. Complementation cell according to claim 14, wherein said elements of the second expression cassette comprise a minimal promoter equipped at its 5' end with 1 to 20 tet O sequences.

32. Complementation cell according to claim 14, wherein said elements necessary for the expression of the second cassette comprise one or more regulatory sequence(s) selected from the group consisting of TAR, RRE, GRE, PRE, ERE and Gal4 UAS sequences or the regulatory sequences of the metallothionein gene or of the bacterial tryptophan lactose or tetracycline operons.

33. Complementation cell according to claim 14, wherein said elements necessary for the expression of the second cassette comprise one or more regulatory sequence(s) from the tetracycline operon, placed upstream of the TATA box of said promoter to give a promoter which is activable by an inducer of the tetracycline transactivator (tTA) type and repressible by tetracycline.

34. Complementation cell according to claim 14, wherein said elements necessary for the expression of the second cassette comprise one or more regulatory sequence(s) from the tetracycline operon placed downstream of the TATA box of said promoter, to give a promoter which is repressible by the tetracycline repressor (Tet R).

35. Method of preparation of an infectious adenoviral particle, comprising:
   (i) introducing an adenoviral vector into a complementation cell according to claim 14, to obtain an infected complementation cell,
   (ii) culturing said transfected complementation cell under suitable conditions to permit the expression of the adenoviral genes and the production of said infectious viral particle; and
   (iii) recovering said infectious adenoviral particle in the cell culture.

36. Complementation cell according to claim 31, wherein said elements of the second expression cassette comprise a minimal promoter derived from the CMV virus (cytomegalovirus) equipped at its 5' end with 7 tet O sequences.

37. Complementation cell according to claim 26, wherein said second expression cassette is a cassette for the expression of the sequences coding for open reading frames 6 and 7 (ORFs 6/7) of the E4 region of an adenovirus.

38. Complementation cell according to claim 27, wherein said second expression cassette is a cassette for the expression of the sequences coding for the DBP protein (DNA binding protein) of the E2 region of an adenovirus.

39. Complementation cell according to claim 27, wherein said second expression cassette is a cassette for the expression of the sequences coding for a temperature-sensitive mutant of the DBP protein of the E2 region of an adenovirus.

40. Complementation cell according to claim 28 for the complementation of an adenoviral vector which is defective for the E1, E2 and E4 functions, comprising:
   (i) a first cassette for the expression of all or part of the E1 region of an adenovirus, placed under the control of the elements necessary for its expression in said complementation cell,
   (ii) a second cassette for the expression of all or part of the E4 region of an adenovirus, placed under the control of the elements necessary for its expression in said complementation cell, and
   (iii) a third cassette for the expression of all or part of the E2 region of an adenovirus, placed under the control of the elements necessary for its expression in said complementation cell,
      said elements of the second and/or third expression cassette comprising a promoter equipped with at least one tet O sequence.

41. Complementation cell according to claim 40, wherein said promoter is from the CMV virus (cytomegalovirus) and is equipped at its 5' end with 7 tet O sequences.

42. Method according to claim 20, wherein said complementation cell is according to claim 25.

* * * * *